United States Patent
Schietinger et al.

(10) Patent No.: US 6,934,040 B1
(45) Date of Patent: Aug. 23, 2005

(54) OPTICAL TECHNIQUES FOR MEASURING LAYER THICKNESSES AND OTHER SURFACE CHARACTERISTICS OF OBJECTS SUCH AS SEMICONDUCTOR WAFERS

(75) Inventors: Charles W. Schietinger, Portland, OR (US); Anh N. Hoang, San Jose, CA (US); Dmitry V. Bakin, San Jose, CA (US)

(73) Assignee: Luxtron Corporation, Santa Clara, CA (US)

( * ) Notice: Subject to any disclaimer, the term of this patent is extended or adjusted under 35 U.S.C. 154(b) by 4 days.

(21) Appl. No.: 10/672,558

(22) Filed: Sep. 26, 2003

Related U.S. Application Data

(60) Division of application No. 09/577,795, filed on May 24, 2000, now Pat. No. 6,654,132, which is a continuation-in-part of application No. 09/317,697, filed on May 24, 1999, now Pat. No. 6,570,662.

(51) Int. Cl.$^7$ ................................................ G01B 11/28
(52) U.S. Cl. ..................... 356/630; 356/600; 356/237.2
(58) Field of Search ................................. 356/630, 625, 356/600, 237.1, 237.2, 73, 445, 446

(56) References Cited

U.S. PATENT DOCUMENTS

| | | | |
|---|---|---|---|
| 4,293,224 A | 10/1981 | Gaston et al. | |
| 5,138,149 A | 8/1992 | Cadet et al. | |
| 5,166,080 A | 11/1992 | Schietinger et al. | |

(Continued)

FOREIGN PATENT DOCUMENTS

| EP | 62190728 | 8/1987 |
|---|---|---|
| EP | 0412728 A2 | 2/1991 |
| EP | 0663265 A1 | 7/1995 |
| EP | 035740 B1 | 5/1996 |
| EP | 0735565 A1 | 10/1996 |
| EP | 0738561 A1 | 10/1996 |

(Continued)

OTHER PUBLICATIONS

Williams, C.S. et al., "Emissivity, Reflectance, Absorptance, and Transmittance," *OPTICS: A Short Course for Engineers & Scientists*, pp. 31–35, (1984).

Litvak, H.E. et al., "Implementing Real–Time Endpoint Control in CMP," *Semiconductor International*, vol. 19, No. 8, pp. 259–264 (Jul. 1996).

Schietinger C., "Wafer Temperature Measurement in RTP," F. Roozeboom (ed.), *Advances in Rapid Thermal and Integrated Processing*, pp. 103–123, (1996) Kluwer Academic Publishers. Printed in the Netherlands.

(Continued)

Primary Examiner—Gregory J. Toatley, Jr.
Assistant Examiner—Roy M. Punnoose
(74) Attorney, Agent, or Firm—Burns, Doane, Swecker & Mathis, LLP

(57) ABSTRACT

A characteristic of a surface is measured by illuminating the surface with optical radiation over a wide angle and receiving radiation reflected from the surface over an angle that depends on the extend of the illumination angle. An emissivity measurement is made for the surface, and, alternatively, if a reflectivity measurement is made, it becomes more accurate. One application is to measure the thickness of a layer or layers, either a layer made of transparent material or a metal layer. A one or multiple wavelength technique allow very precise measurements of layer thickness. Noise from ambient radiation is minimized by modulating the radiation source at a frequency where such noise is a minimum or non-existent. The measurements may be made during processing of the surface in order to allow precise control of processing semiconductor wafers, flat panel displays, or other articles. A principal application is in situ monitoring of film thickness reduction by chemical-mechanical-polishing (CMP).

15 Claims, 15 Drawing Sheets

U.S. PATENT DOCUMENTS

| | | |
|---|---|---|
| 5,166,525 A | 11/1992 | Rodgers et al. |
| 5,190,614 A | 3/1993 | Leach et al. |
| RE34,425 E | 11/1993 | Schultz |
| 5,292,605 A | 3/1994 | Thomson |
| 5,308,447 A | 5/1994 | Lewis et al. |
| 5,362,969 A | 11/1994 | Glenn |
| 5,416,594 A | 5/1995 | Gross et al. |
| 5,433,651 A | 7/1995 | Lustig et al. |
| 5,475,221 A | 12/1995 | Wang |
| 5,486,701 A | 1/1996 | Norton et al. |
| 5,499,733 A | 3/1996 | Litvak |
| 5,555,474 A | 9/1996 | Ledger |
| 5,564,830 A | 10/1996 | Bobel et al. |
| 5,568,252 A | 10/1996 | Kusuda et al. |
| 5,608,526 A | 3/1997 | Piwonka-Corle et al. |
| 5,609,511 A | 3/1997 | Moriyama et al. |
| 5,625,459 A * | 4/1997 | Driver ..................... 356/446 |
| 5,640,242 A | 6/1997 | O'Boyle et al. |
| 5,659,397 A | 8/1997 | Miller et al. |
| 5,663,797 A | 9/1997 | Sandhu |
| 5,695,660 A | 12/1997 | Litvak |
| 5,717,608 A | 2/1998 | Jensen |
| 5,724,144 A | 3/1998 | Muller et al. |
| 5,769,540 A | 6/1998 | Schietinger et al. |
| 5,786,886 A | 7/1998 | Litvak et al. |
| 5,825,495 A | 10/1998 | Huber |
| 5,828,460 A | 10/1998 | Lucovsky et al. |
| 5,835,225 A | 11/1998 | Thakur |
| 5,838,447 A | 11/1998 | Hiyama et al. |
| 5,838,448 A | 11/1998 | Aiyer et al. |
| 5,851,135 A | 12/1998 | Sandhu et al. |
| 5,872,633 A | 2/1999 | Holzapfel et al. |
| 5,899,792 A | 5/1999 | Yagi |
| 6,614,529 B1 * | 9/2003 | Tang ..................... 356/630 |

FOREIGN PATENT DOCUMENTS

| | | |
|---|---|---|
| EP | 0824995 A1 | 2/1998 |
| GB | 2009922 A | 6/1979 |
| JP | 62190728 | 8/1987 |
| JP | 62190728 A | 8/1987 |
| JP | 08339982 | 12/1996 |
| WO | WO9325893 | 12/1993 |
| WO | W9407110 | 3/1994 |
| WO | WO9518353 | 7/1995 |
| WO | WO9725660 | 7/1997 |
| WO | W9858400 | 12/1998 |
| WO | W9901745 | 1/1999 |
| WO | W9923479 | 5/1999 |

OTHER PUBLICATIONS

Schietinger, C., "Wafer Emissivity in RTP," F. Roozeboom (ed.), *Advances in Rapid Thermal and Integrated Processing*, pp. 125–141, (1996) Kluwer Academic Publishers, Printed in the Netherlands.

Fang, S.J. et al., "Control of Dielectric Chemical Mechanical Polishing (CMP) Using an Integerometry Based Endpoint Sensor," *Proceedings of the IEEE 1998 International Inconnect Technology Conference*, Hyatt Regency Hotel, San Francisco, CA, pp. 98–76 to 98–78 (Jun. 1–3, 1998).

Bibby, T. et al., "Endpoint Detection for CMP," *Journal of Electronic Materials*, vol. 27, No. 10, pp. 1073–1081 (1998).

Berman, M. et al., "Review of In Situ & In–line Detection for CMP Applications," *Semiconductor Fabtech –8th Edition*, Article contains eight pages.

Xu, H., et al., "Emissivity of Rough Silicon Surfaces: Measurement and Calculations," *Materials Research Society*, Symposium Proceedings vol. 387, symposium help Apr. 17–20, 1995 –San Francisco, California, pp. 29–34.

Nicodemus, F., "Directional Reflectance and Emissivity of an Opague Surface," *Applied Optics*, vol. 4, No. 7, Jul. 1965, pp. 767–773.

* cited by examiner

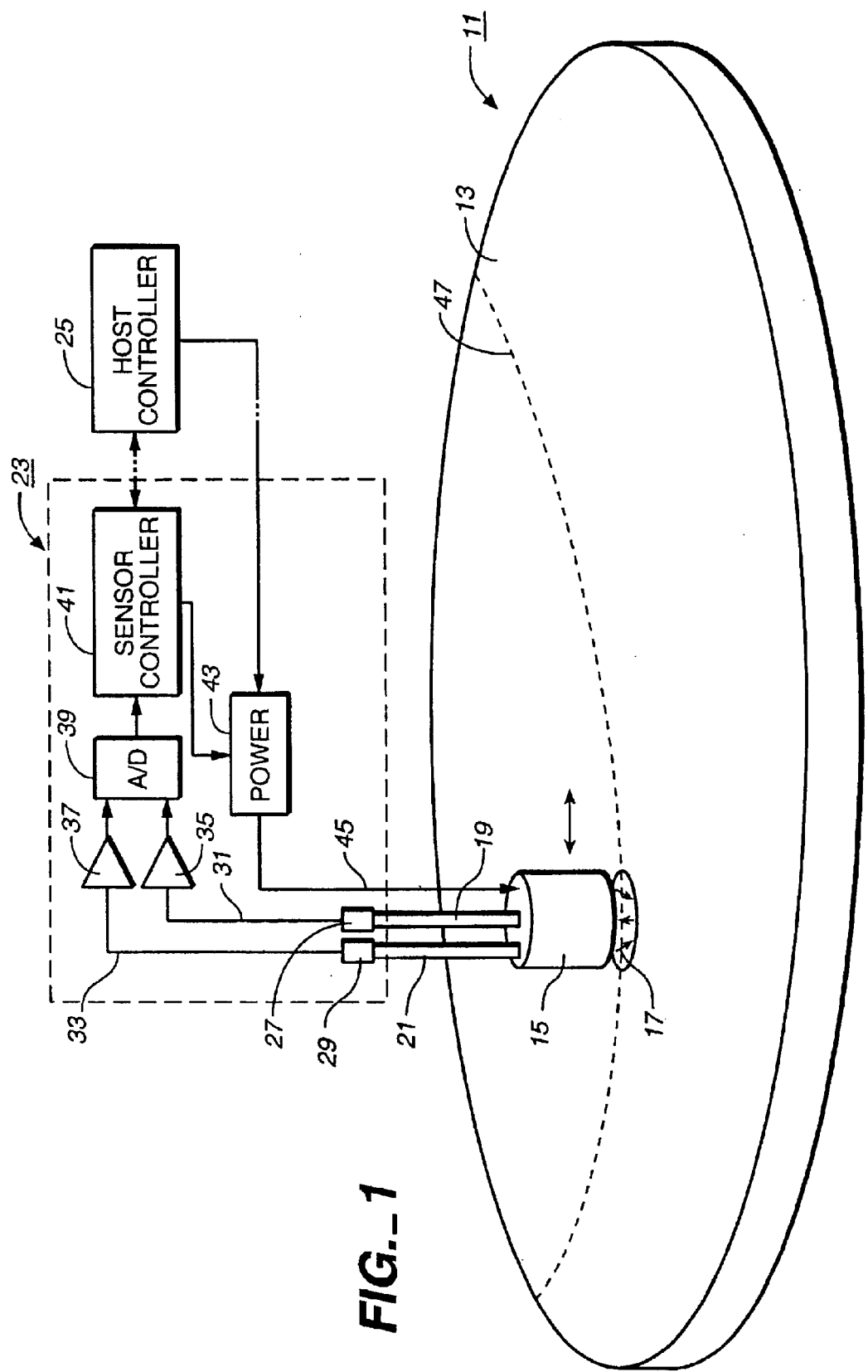
FIG._1

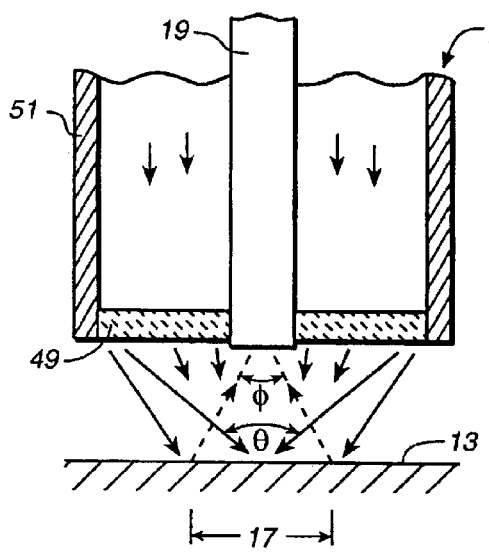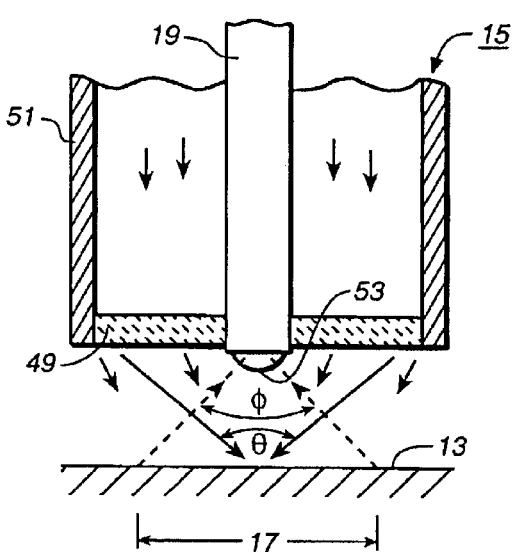
FIG._2  FIG._3

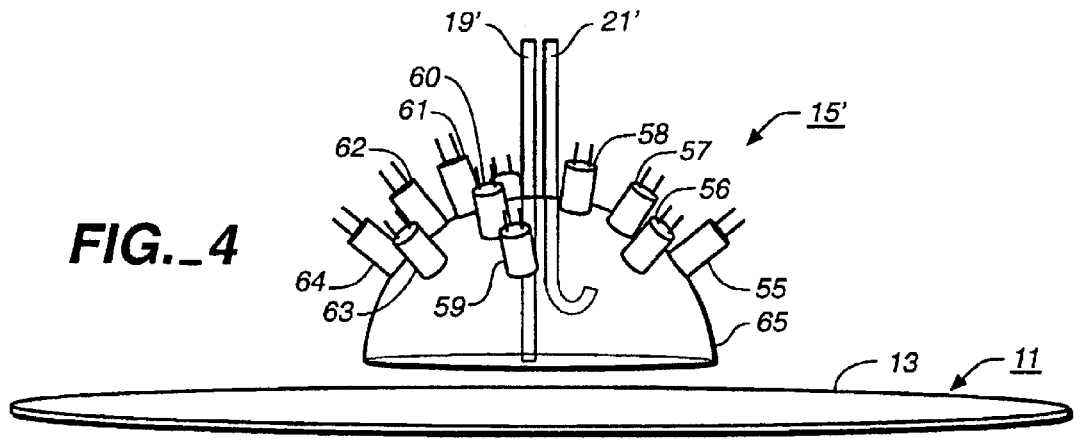
FIG._4
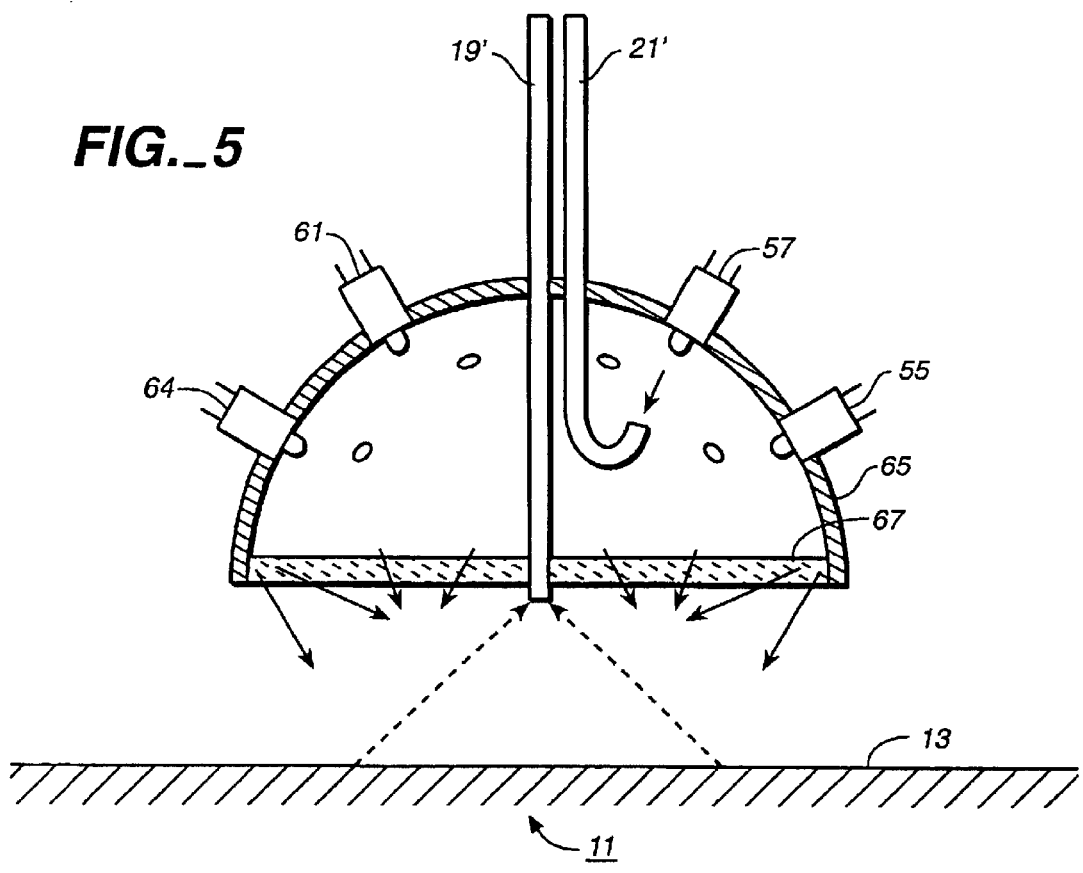
FIG._5

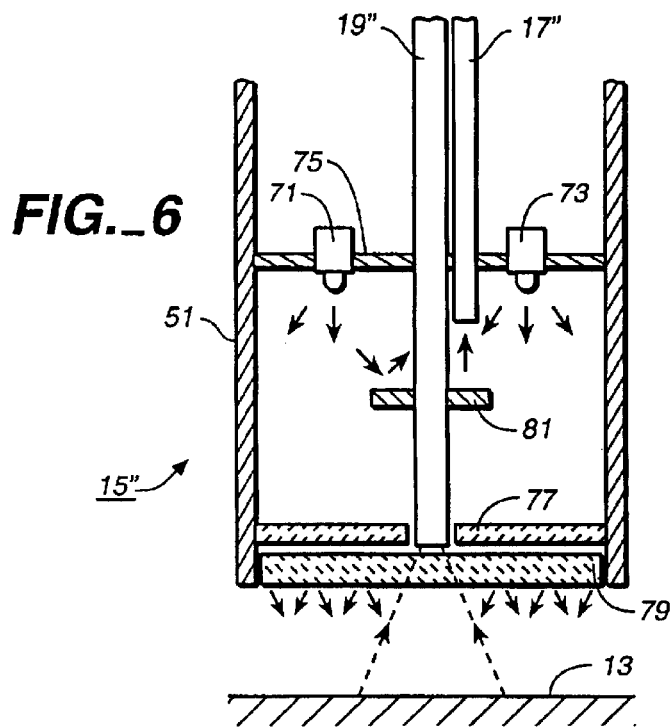
FIG._6
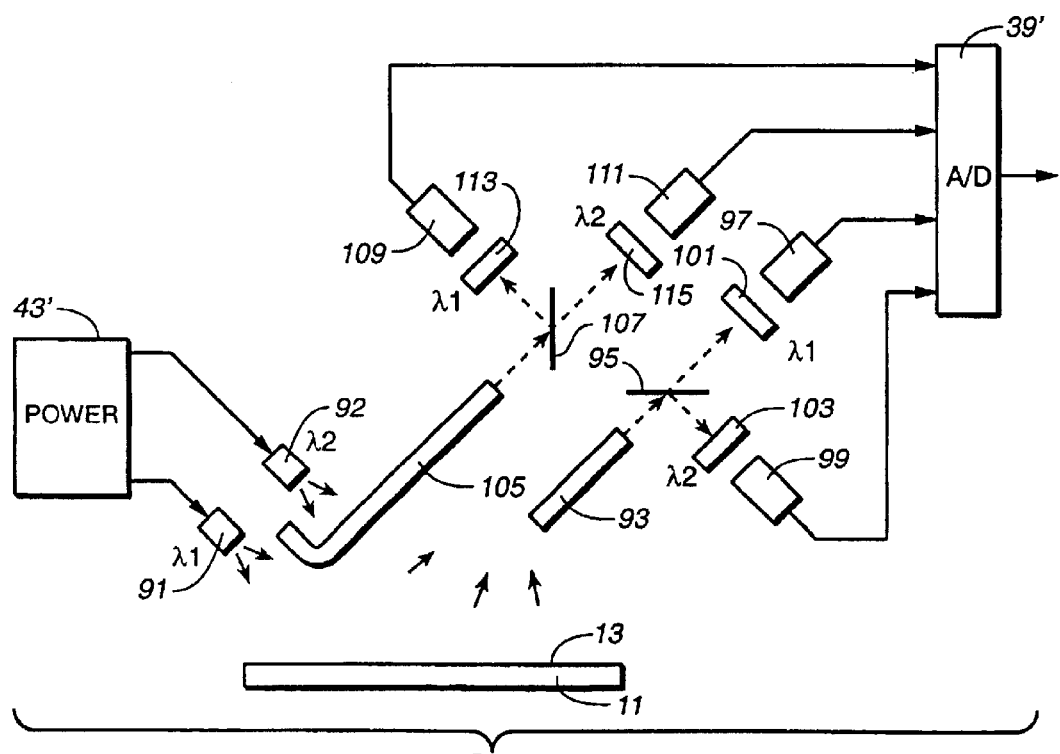
FIG._7

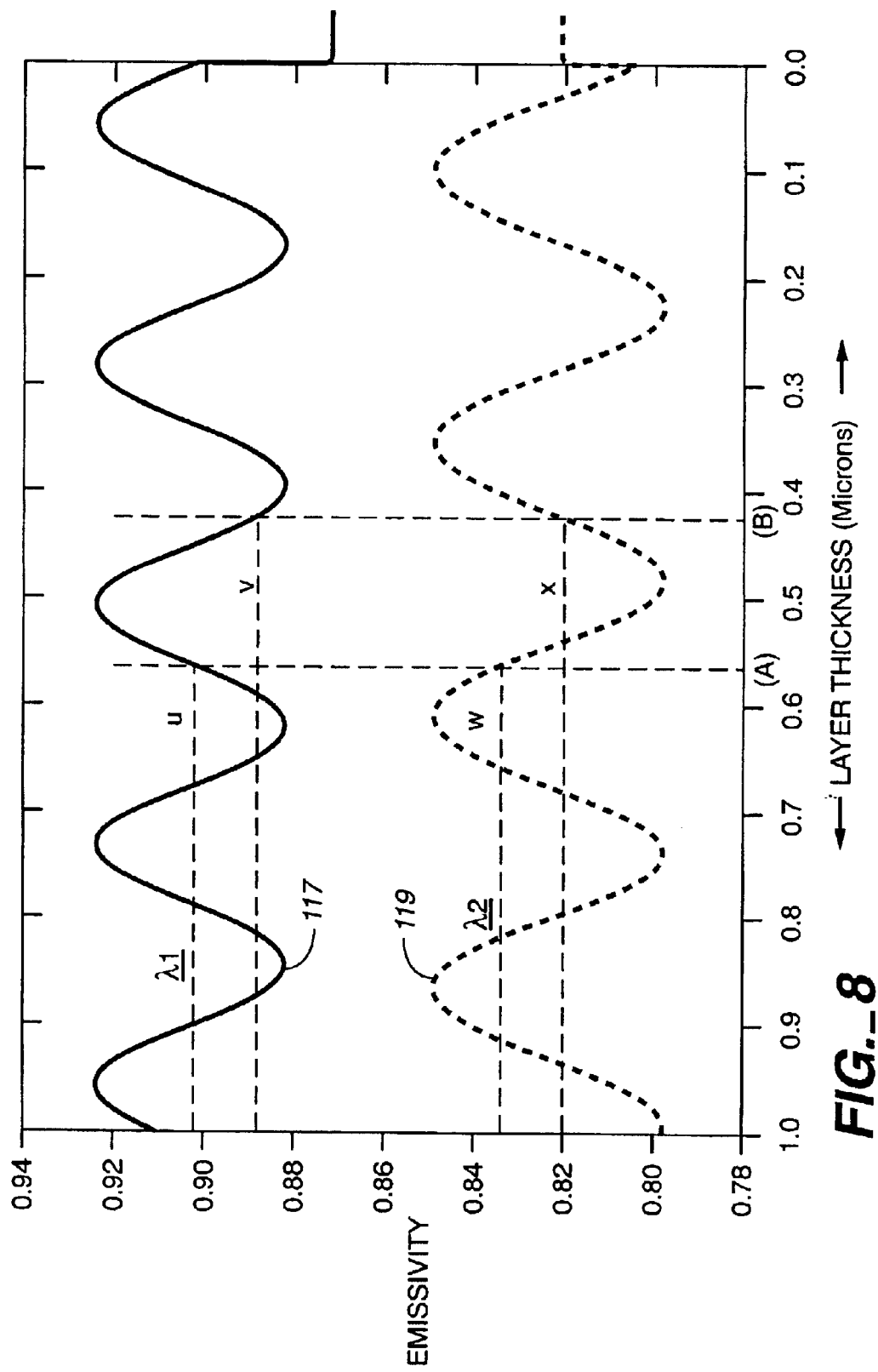
FIG._8

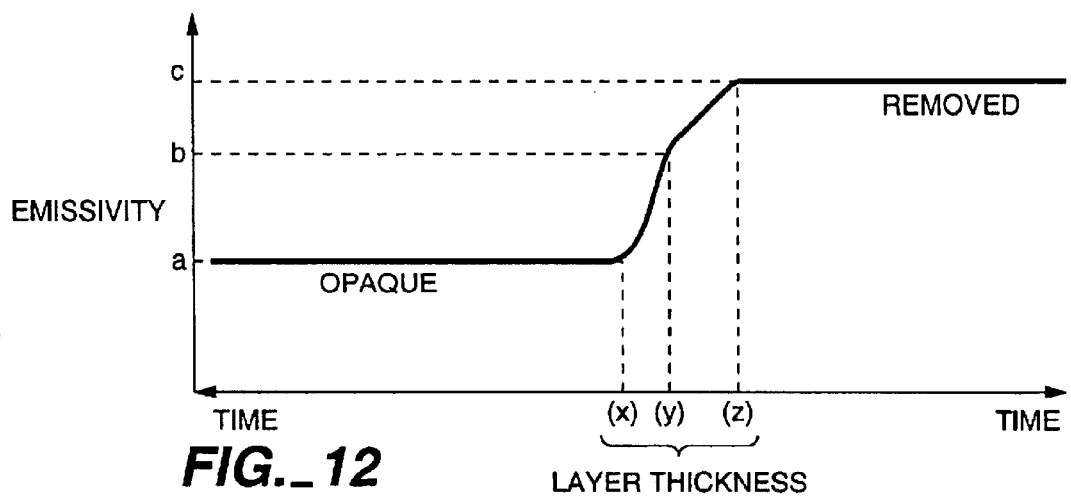

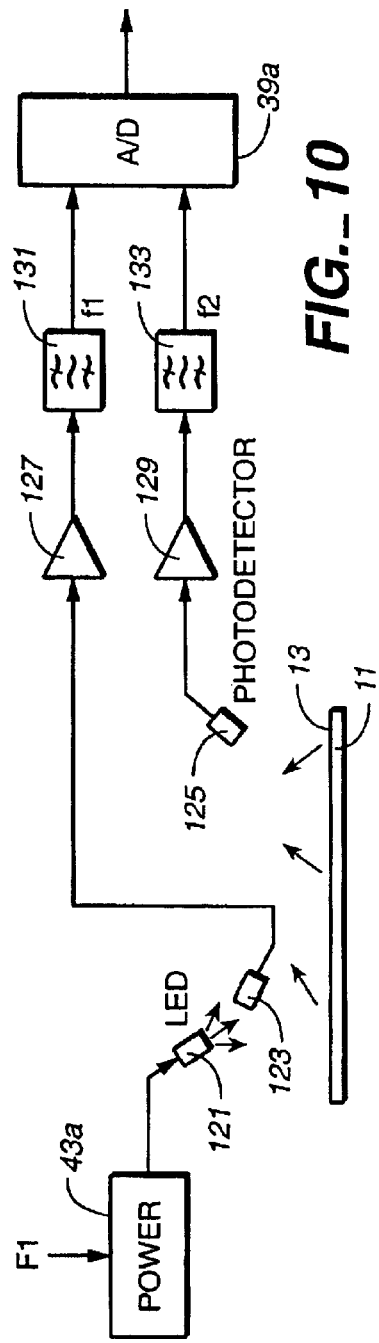
FIG._10
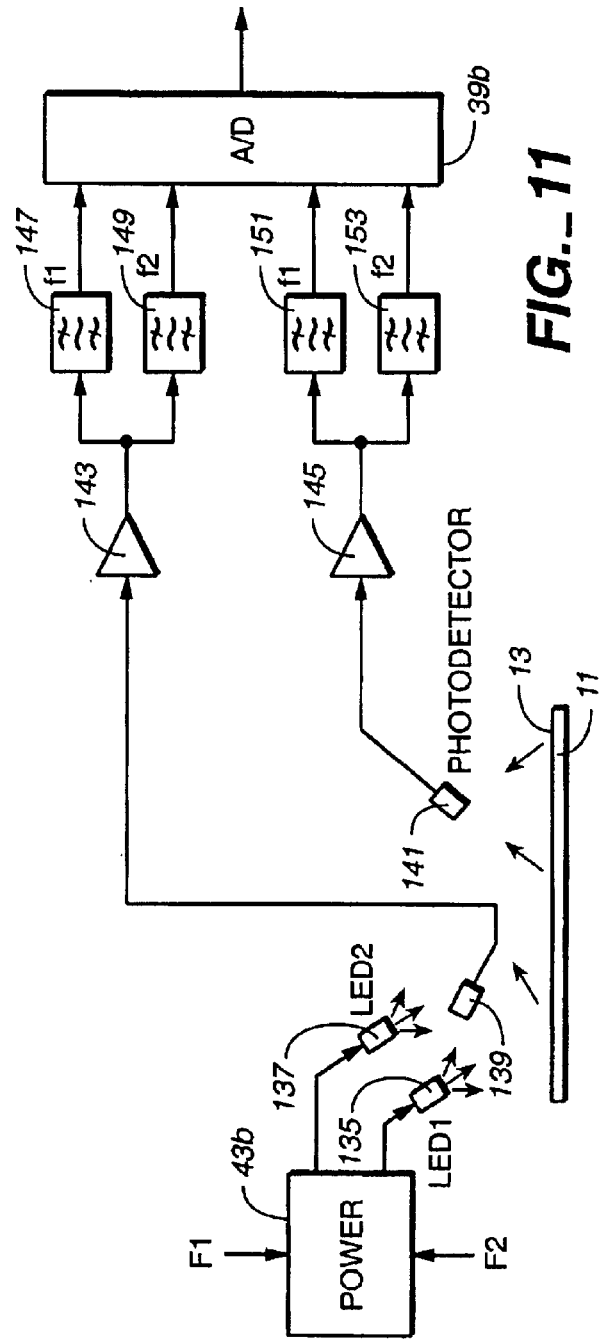
FIG._11

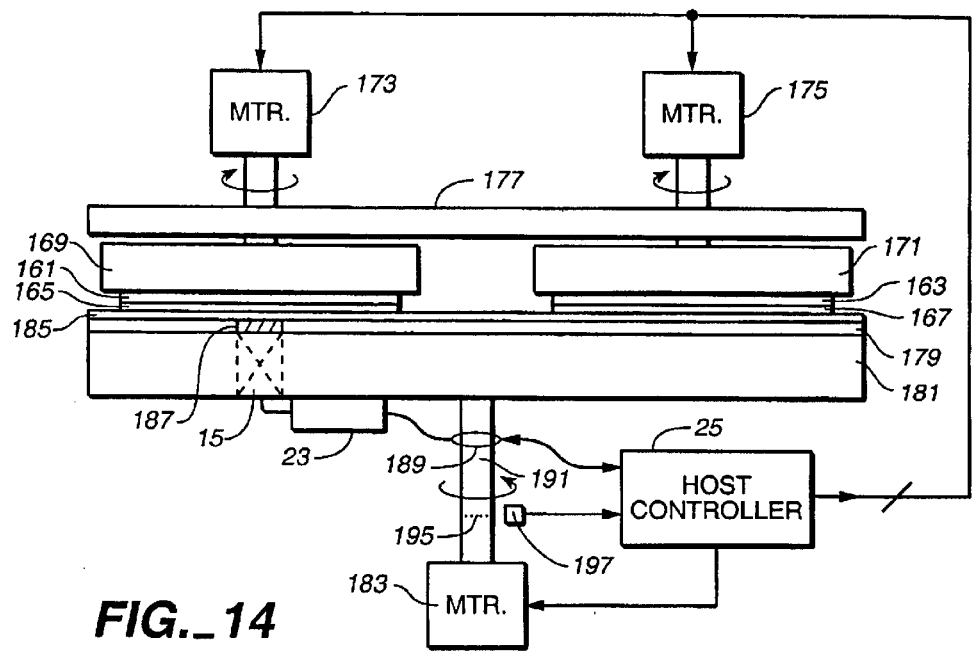
FIG._14
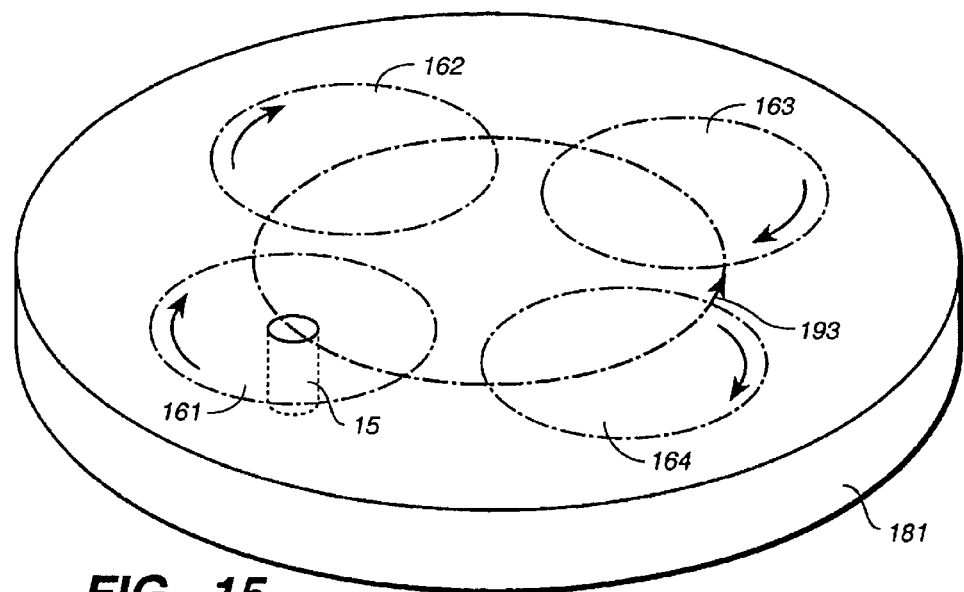
FIG._15

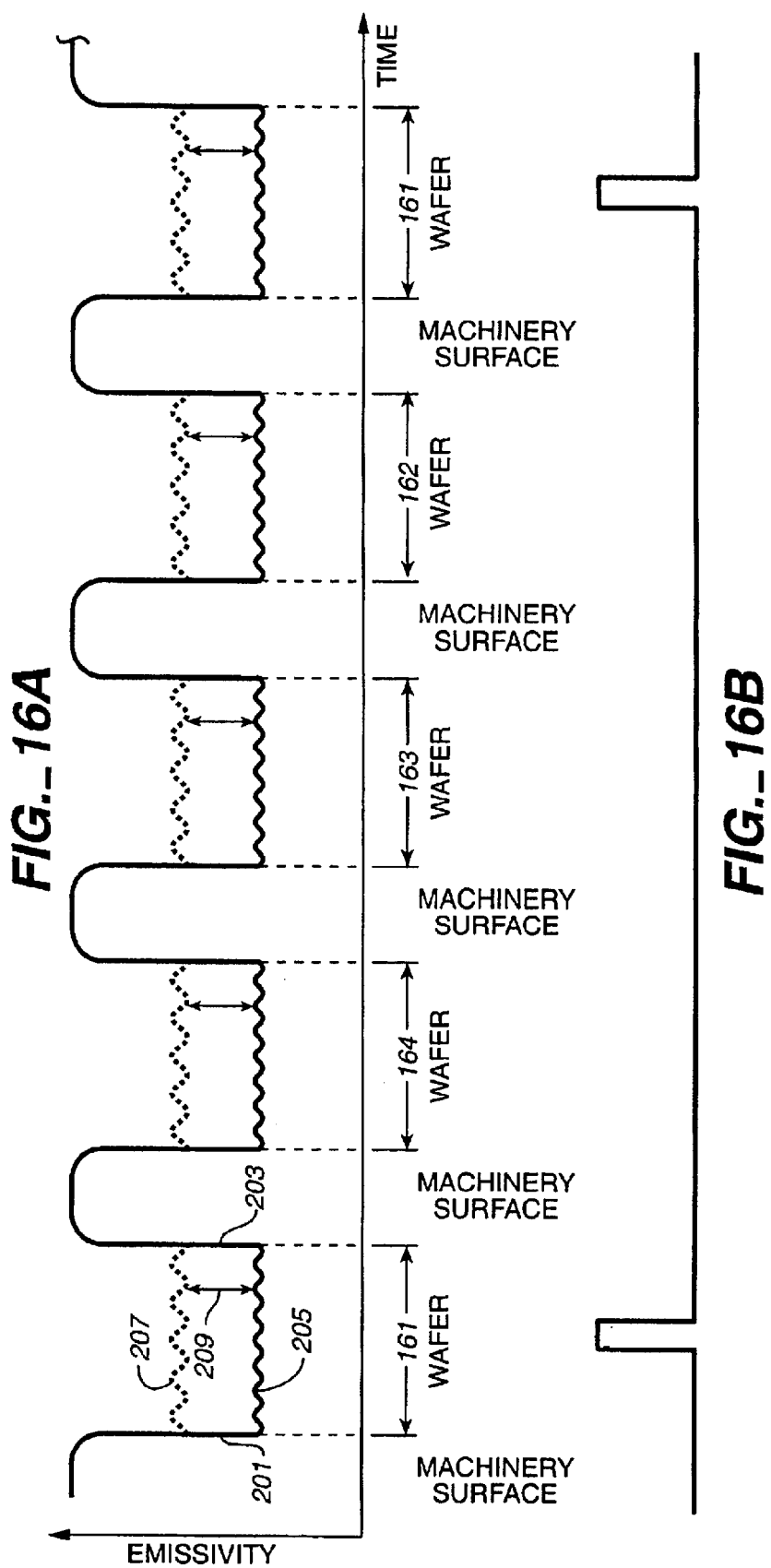

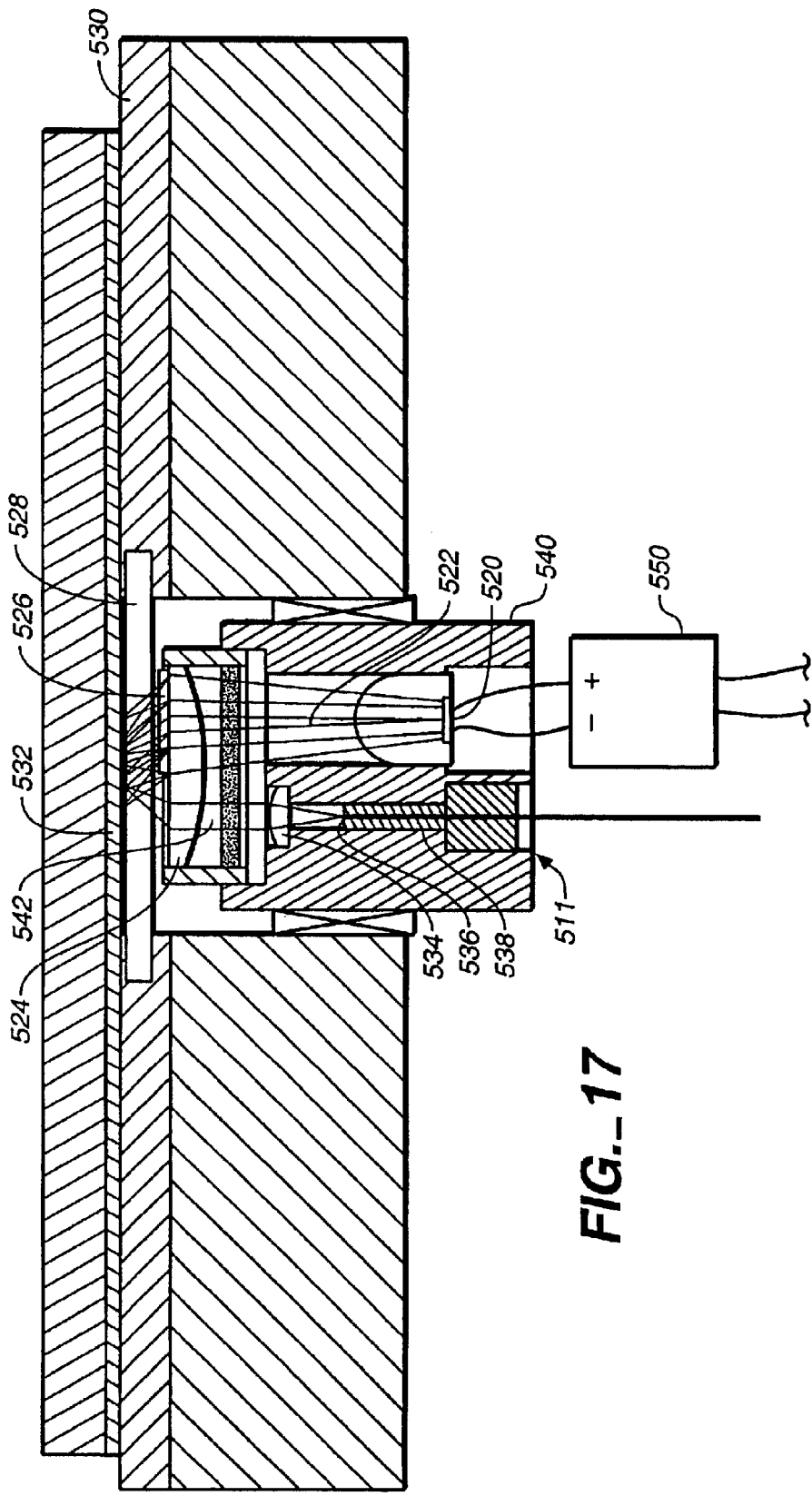
FIG._17

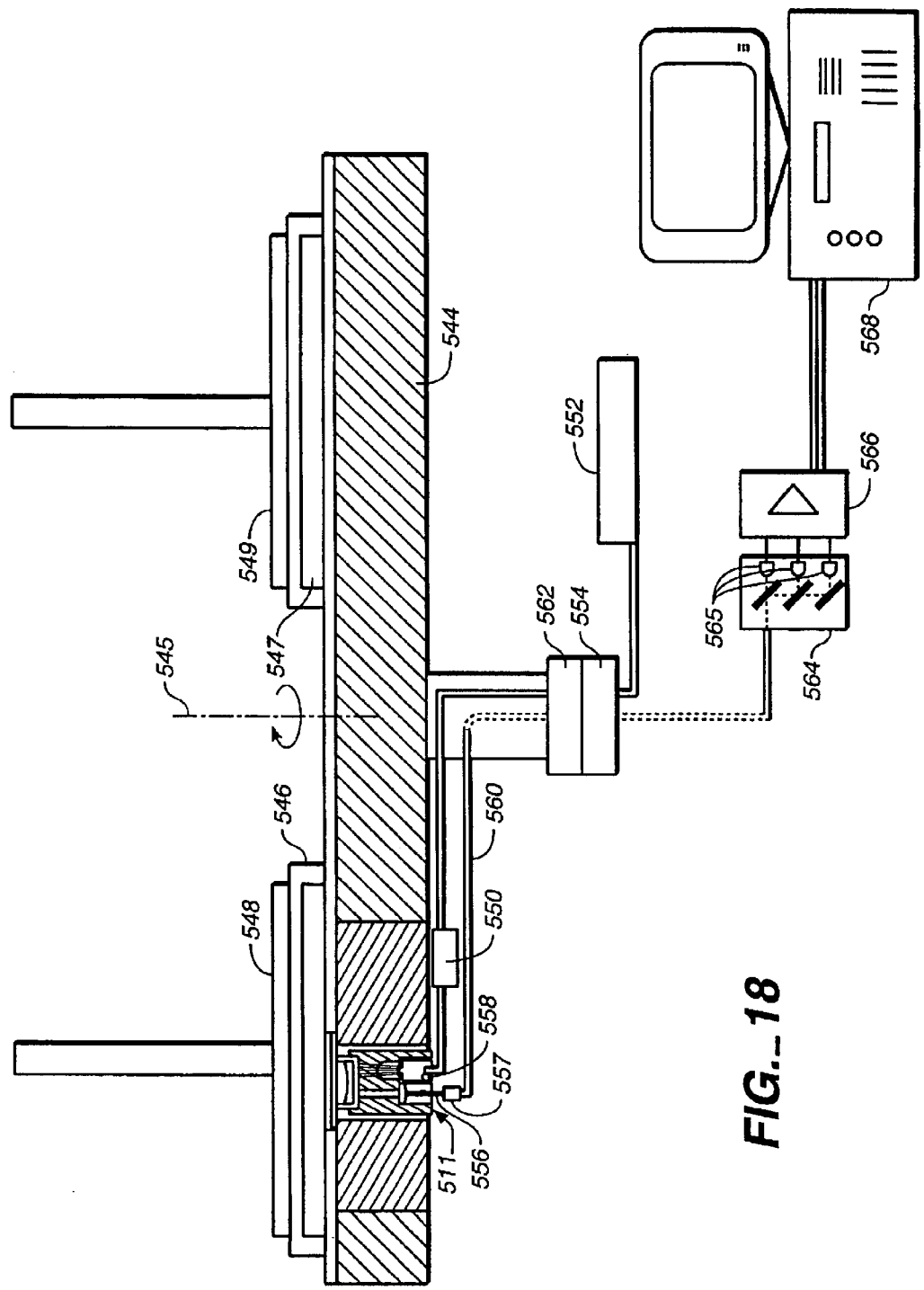
FIG._18

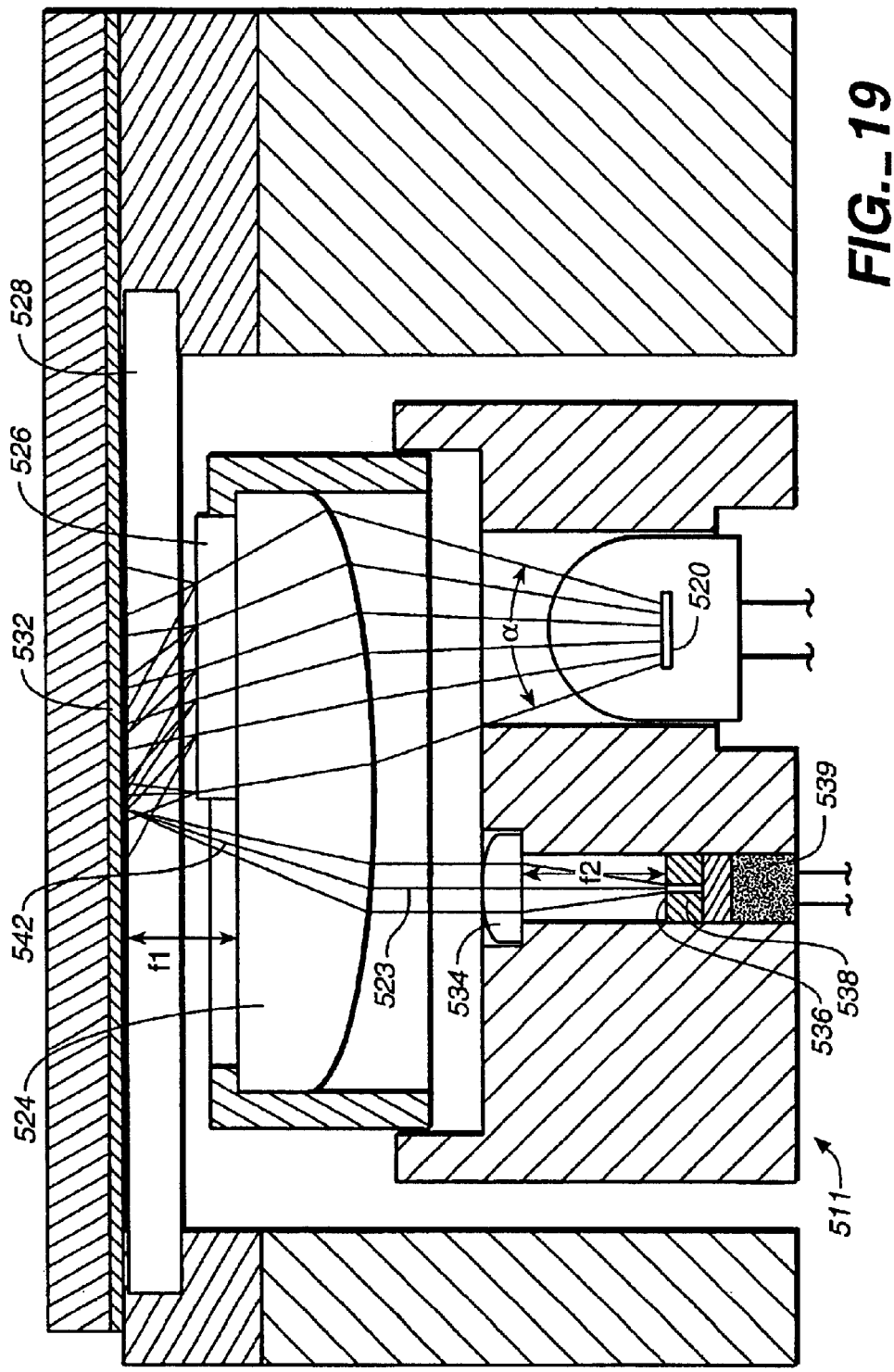
FIG._19

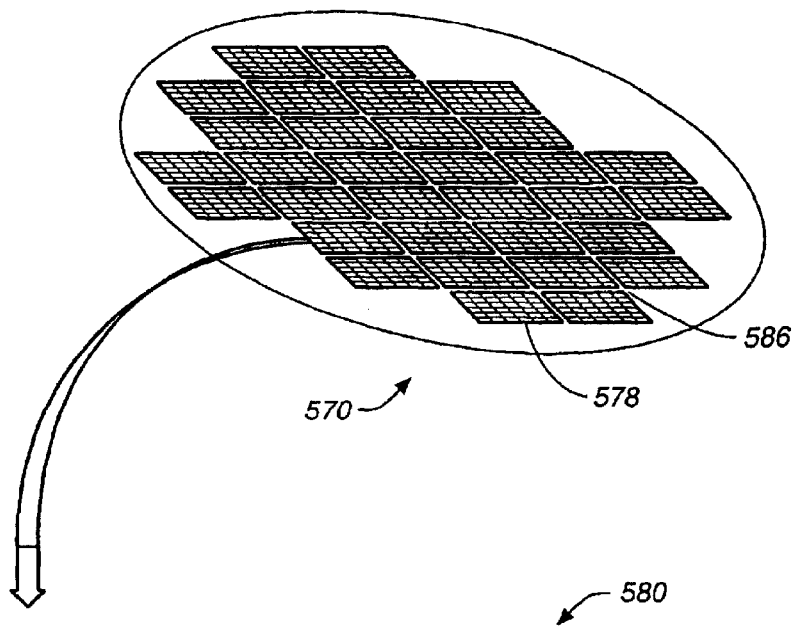
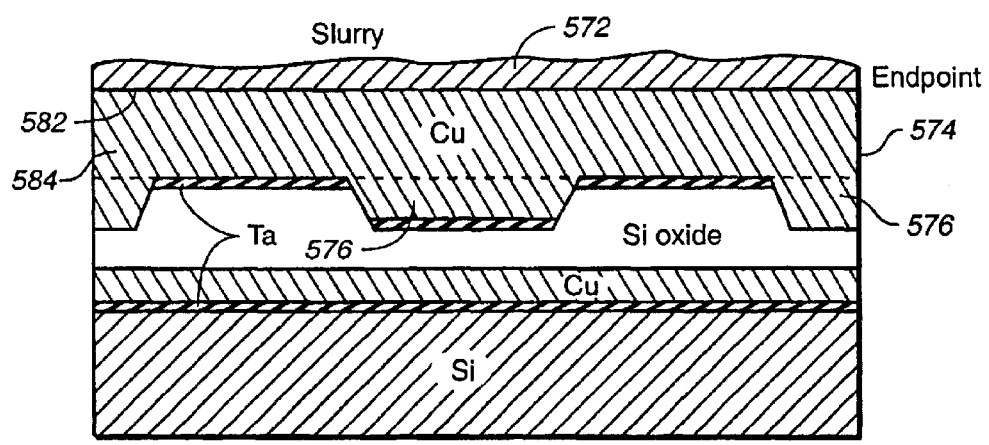
FIG._20

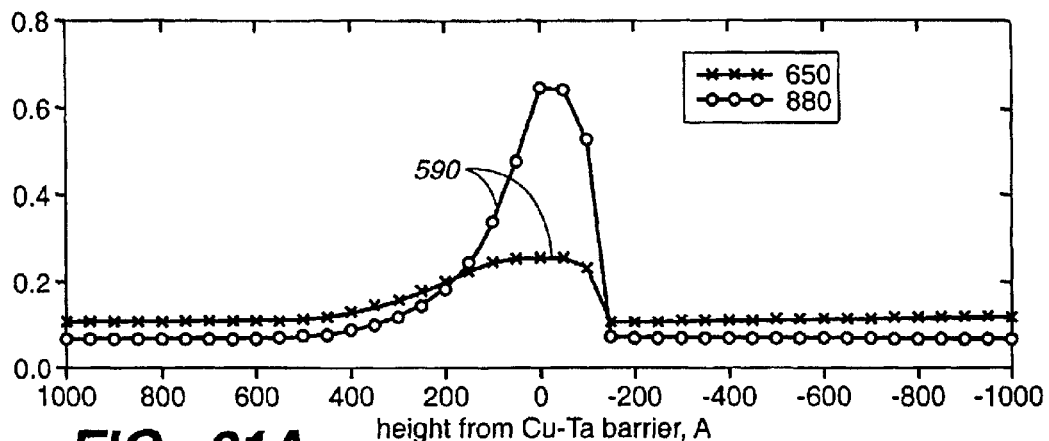
FIG._21A
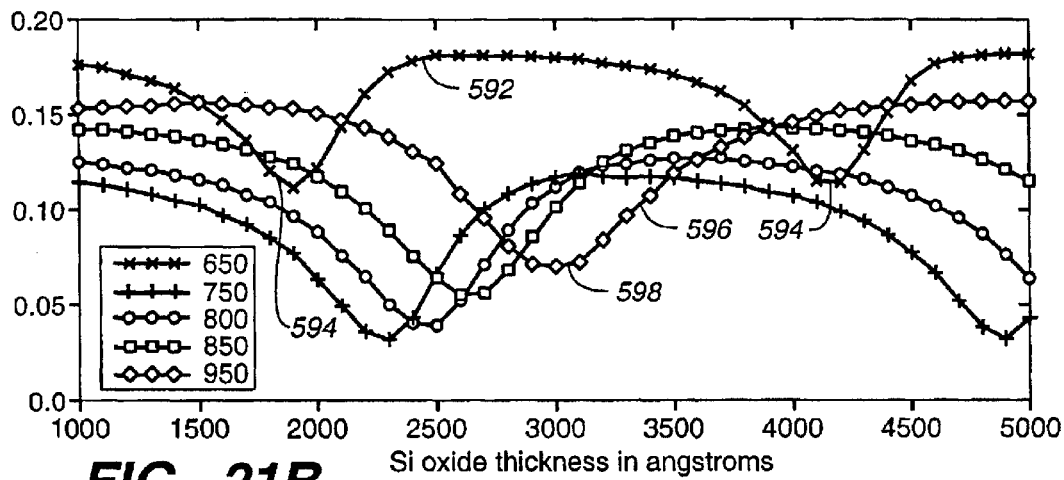
FIG._21B
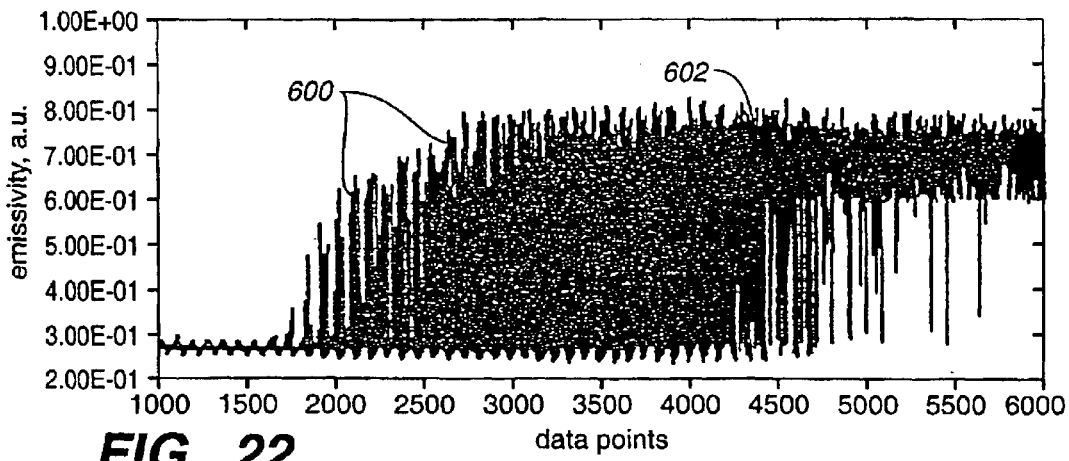
FIG._22

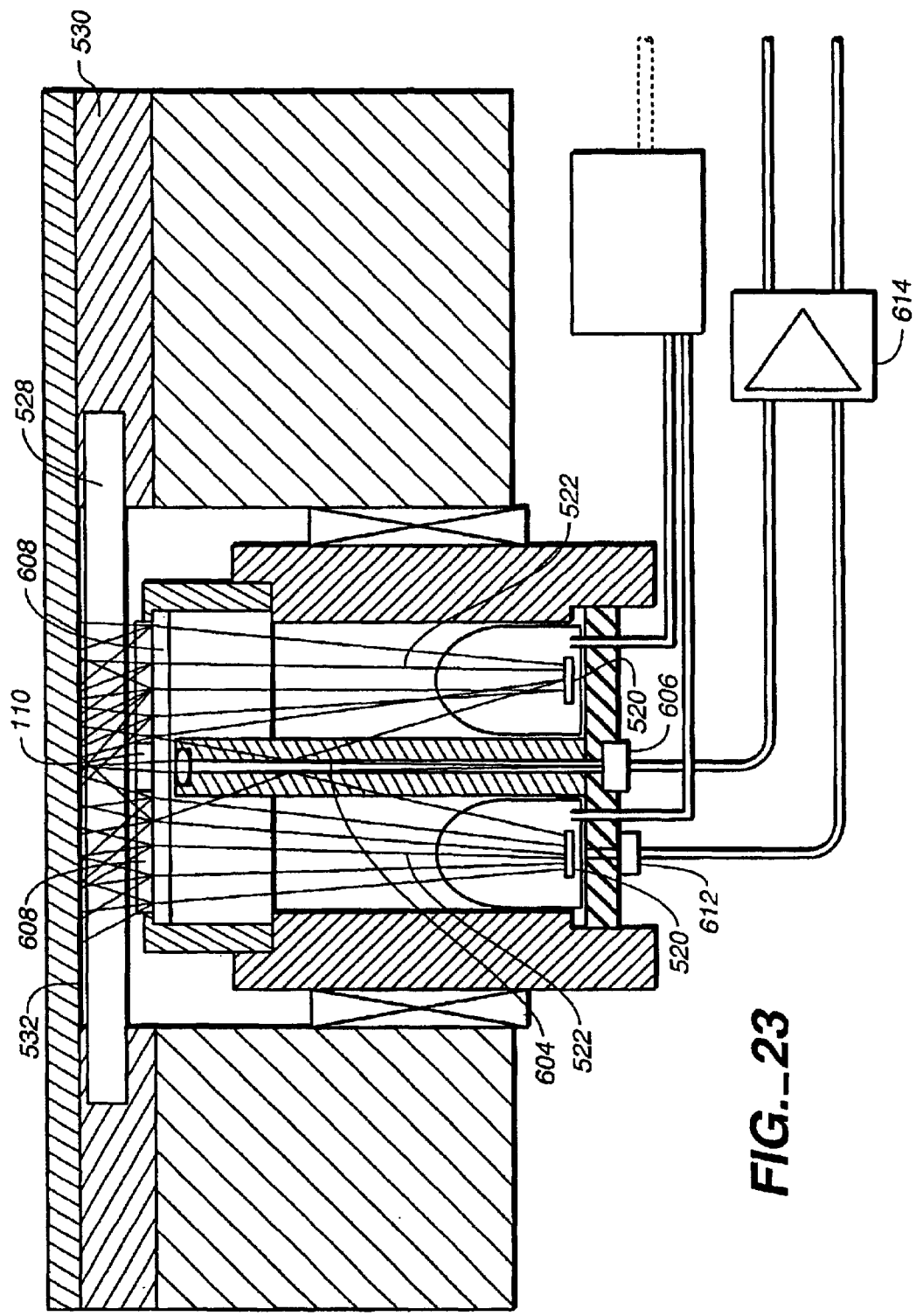
FIG._23

OPTICAL TECHNIQUES FOR MEASURING LAYER THICKNESSES AND OTHER SURFACE CHARACTERISTICS OF OBJECTS SUCH AS SEMICONDUCTOR WAFERS

CROSS-REFERENCE TO RELATED APPLICATIONS

This application is a divisional of application Ser. No. 09/577,795, filed May 24, 2000, now U.S. Pat. No. 6,654,132 which in turn is a continuation-in-part of application Ser. No. 09/317,697, filed May 24, 1999, now U.S. Pat. No. 6,570,662 B1, which issued on May 27, 2003, which applications are incorporated herein in full by this reference.

BACKGROUND OF THE INVENTION

This invention relates generally to techniques for determining conditions of surfaces, and, more specifically, to doing so by measuring a characteristic of the reflectivity and/or emissivity of surfaces. An example application is the measurement of the thickness of a film on a substrate, such as a film that is formed or removed from a semiconductor wafer during the fabrication of integrated circuits. The thickness measurement is made either simultaneously with the film processing (in situ) or thereafter (in line). More specific applications include in situ measurements of the thickness of a film being reduced or removed by techniques such as wet etching, plasma etching, spin etching or chemical-mechanical-polishing (CMP).

As a result of the development of new semiconductor processing techniques and a steadily shrinking minimum semiconductor element size, a need exists to constantly improve techniques of monitoring and measuring the results of processing, and also to develop new ones. The trend is to make as many measurements of semiconductor wafers as possible in situ, which is usually more difficult to do than as a separate step after the processing. An example of one recent development is described in U.S. Pat. No. 5,769,540, wherein the reflectivity of a surface is measured, from which its emissivity and/or temperature can be determined without contacting the surface. The emissivity measurement is also usable to determine the thickness of a film carried by the substrate. These techniques are particularly useful for making in situ measurements during rapid thermal processing (RTP). Another development, described in U.S. Pat. No. 5,695,660, measures the thickness or level of planarization of both dielectric and metal layers in situ by optical or thermal techniques during etching or CMP, including making the measurements through the back side of the wafer. When applied to CMP, an optical signal communicates with a wafer being processed through an optical window provided in one of the moving elements such as the wafer carrier. In published international (PCT) application no. WO 97/25660, multiple sensors are carried by a moving component of a CMP machine, with a wireless communication of measurements and control signals provided between the sensors and a host control station. Other patent documents of interest include U.S. Pat. Nos. 5,138,149, 5,190,614, 5,166,525, 5,292,605, 5,308,447, 5,362,969, 5,717,608 and 5,786,886, and PCT publication no. WO93/25893. Each of the foregoing patent publications is from Luxtron Corporation of Santa Clara, Calif., the assignee hereof, and is incorporated herein in its entirety by this reference.

It is a principal object of the present invention to provide further improvements to methods and instruments for optically measuring characteristics of surfaces, such as surfaces of circuit structures partially formed on semiconductor wafers or flat panel displays.

It is a more specific object of the present invention to provide such further improvements to monitor the effects CMP processing.

It is another object of the present invention to provide improved optical methods and instruments for measuring the thickness of layers of dielectric, semiconductor or metal materials carried by a substrate.

It is a further object of the present invention to carry out the foregoing objects simultaneously with processing the surface or layer being monitored (in situ).

It is an even more specific object of the present invention to accurately measure the changing thickness of a layer carried by a substrate, such as a semiconductor wafer, while being processed (in situ) to increase or decrease the layer thickness.

SUMMARY OF THE INVENTION

These and additional objects of the present invention are realized by the various aspects of the present invention, which are briefly and generally summarized.

A surface being monitored is illuminated by optical radiation with rays of the incident radiation spread over a wide angle to form a radiation field modified by the surface that is collected over an angle that is as large as practical, and then detected by a sensor, which collection angle may be narrowed, when there is a reason to do so, as the illumination angle becomes very large. The angles of optical radiation illumination and collection are made sufficiently wide so that variations in an optical radiation path and/or of the surface being monitored, other than of the surface optical characteristic of interest, that occur over time or between different copies of the surface are minimized or substantially eliminated in order to improve the accuracy of the resultant measurements. In typical applications, the incident radiation is preferably spread over an angle of at least 45 degrees and up to 180 degrees when striking the surface being monitored, and is also preferably collected over an angle of 45 degrees or more, and up to 180 degrees. However, as the illumination angle is increased, the collection angle can be made narrower. The collected radiation is detected, and the detected radiation is processed to monitor a desired characteristic of the surface. Specific structures of sensors include use of an optical radiation spreading element, such as a diffuser or multi-pass reflector, positioned near to the surface being monitored, and an optical collection element, such as an end of an optical fiber or a lens, is positioned to receive the radiation after being modified by the surface, such as by reflection from the surface. Random or pseudo-random scattering of the illumination radiation is preferred, such as occurs when the optical radiation incident on the surface being monitored has passed through ground glass.

The wide angle illumination and detection significantly reduces the effects of variations in scattering of the optical signals that can occur independently of the quantity desired to be measured. The incident optical radiation, and that modified by the surface being monitored, can be scattered varying amounts that depend upon the surface, angles that the radiation strikes the surface and optical elements, changes over time, and other causes. If the viewing angle is too narrow for a given angular extent of the illumination, for example, any variation in the amount of incident radiation that is scatted into the narrow viewing angle because of differences in scattering properties across the surface being monitored or between different surfaces, versus that which is scattered over wider angles out of view, causes the detected optical signal to vary. Significant variations can also occur when the surface is being viewed through a liquid layer, such as an etchant or slurry, that changes its thickness and other characteristics over time. These factors often cause the measurement signal to have significant amounts of undesired noise. But if the surface is illuminated and viewed over wide angles relative to that through which the incident radiation is scattered by the surface, any liquid etchant on it and by the optical elements, this source of noise is significantly reduced. It is reduced further when the surface is illuminated over wide angles. Illumination and detection over a full hemisphere is ideal but significant improvements are made when lesser angles in the range given above are utilized.

If a surface is illuminated with radiation over a very wide angle, such as 80 degrees or more, the surface modified radiation may be gathered for detection over a small angle, such as 25 or 15 degrees or less, and still provide the advantages described above. A small collection angle is often desired for other purposes, such as to increase the depth of focus of the collection optics, allow practical sized collection optics, increase the sensitivity of the measurement to the thickness of a films being monitored, in those applications, and/or to focus on a very small spot on the surface being monitored.

The term "optical radiation" is used in this application to mean electromagnetic radiation in a continuous wavelength range including visible and near visible infrared and ultraviolet wavelengths, generally considered to extend from about 0.2 to about 4 microns. Monitoring the optical radiation modified by a surface usually also includes monitoring the level of radiation incident upon the surface so that the reflectivity or emissivity of the surface, or a related quantity, can be calculated either as the ultimate surface characteristic to be determined or as an intermediate quantity used to calculate some other surface characteristic. By making the measurements in a defined radiation wavelength range and with the geometric constraints discussed above, resulting calculations of the reflectivity or emissivity of the surface are highly meaningful because they are independent of changing conditions unrelated to surface reflectivity and emissivity. The calculation of emissivity is preferred because it is understood in the scientific community to be independent of the geometry, wavelength and other factors that can cause undesired variations in optical measurements.

When a layer of material being formed on or removed from a substrate, in whole or in part, is being monitored, it is preferably illuminated and viewed in the above described manner. An endpoint to the complete removal of a layer is one characteristic of the surface that may be determined. Another characteristic is the thickness of the layer, either in relative or absolute terms. Because surface reflectivity or emissivity is being determined with the effects of varying measurement conditions being minimized, the thickness of a layer can be determined with a high degree of accuracy by a look-up table, model or other relationship between the reflectivity or emissivity and thickness.

When the monitored layer is a metal or other generally opaque material, its reflectivity and emissivity are directly related to the thickness of the layer if the layer is thin enough to be at least partially transparent. For example, when a metal layer is being removed from a substrate, the layer's reflectivity or emissivity, when measured by the techniques summarized above, is directly related to the thickness of the metal layer once it has become thin enough to be semi-transparent. A metal film on a semiconductor wafer is semi-transparent when its thickness is less than about 500 to 1500 Angstroms, depending on the metal and the wavelength of radiation used. Therefore, for such thin metal layers, their thicknesses can be determined from a look-up table or set of functions that relate the measured reflectivity or emissivity with the layer's thickness. This makes it possible to measure and control the thicknesses of thin metal films with precision. Once the metal film is completely removed, then the optical properties being measured are those of the layers under the metal film. The measurement of the reflectivity or emissivity of a metal layer can be conducted with one or more wavelengths of optical radiation.

The thickness of a layer of transparent material, such as a dielectric, can be monitored throughout a range of its entire thickness by viewing a signal resulting from interference of a portion of the incident optical radiation reflected from an outside surface from which material is being removed and another portion of the incident radiation reflected from some other interface in the structure of the substrate and layer. A given table or set of functions are used to relate specific values of the interference signal with layer thicknesses. Interference signals are preferably generated in at least two different wavelengths of optical radiation. Precise measurements of the thickness of a transparent layer are then obtainable without ambiguity under many circumstances when the two or more optical radiation wavelengths and ranges of layer thicknesses are suitable. In other cases, such precision additionally requires knowledge of the approximate layer thickness, as determined by observation or otherwise, in order to obtain a precise measurement of the transparent layer's thickness without ambiguity.

When two or more wavelengths of radiation are used to illuminate a layer, the radiation can be generated by separate narrow bandwidth radiation sources, such as light emitting diodes (LEDs), and then the uniquely responsive to one of the source wavelengths. Alternatively, or in combination, the two or more radiation sources are each modulated with a unique frequency. Electrical signals obtained from a single or multiple radiation receiving photodetectors are then filtered to pass the source modulating frequencies in order to obtain a separate signal for each of the illumination wavelengths. The frequencies of modulation are preferably selected to be different from that of any ambient radiation or electrical noise that might be present in the environment in which the measurements are being taken, thereby to significantly reduce adverse effects of any such ambient radiation and noise. The radiation source modulation and photodetector signal filtering technique can also be used when a single optical radiation is directed at the surface being monitored in order to similarly reduce the effects of any ambient radiation and electrical noise that might be present at different frequencies from the modulating frequency.

Although the techniques summarized above are useful to measure a surface characteristic in-line or off-line when processing of the surface is not taking place, it is usually preferable to apply these techniques to in situ monitoring. This saves the extra steps necessary to make the measurements and provides the results in real time. The processing can then be controlled from the measurements, either automatically or by providing the measurements to an operator who then adjusts the processing. One specific processing method where these measurement techniques are particularly useful is CMP, where one or more substrates (such as semiconductor wafers) are held by a carrier, and their exposed surfaces moved across a polishing pad carried by a platen. A slurry of abrasive particles and a chemical etchant is usually also used on the pad. One or more optical radiation sensors, preferably of the wide radiation angle type described above, are installed in either the carrier, if the processing is being viewed from the back side of the substrates, or in the platen, if being viewed from the front side of the substrates. The front side of the wafers can also be periodically viewed in some CMP machines when the wafers are being loaded into or unloaded from the CMP machine, or are periodically moved off the platen within the CMP machine during the CMP process.

When a layer of metal (such as copper, aluminum, tungsten or cobalt) is being removed from a semiconductor surface to leave conductive lines in trenches of an underlying dielectric material layer, the sensitivity to the detection of endpoint by monitoring large areas of the surface is low since the metal remains mainly in the trenches at endpoint. These remaining metal lines can extend over a large percentage of the area of integrated circuit (I.C.) devices being formed on the substrate, so that a reflected signal does not change very much upon reaching endpoint. However, if small areas of the surface in between such I.C. devices are monitored, the sensitivity of endpoint detection increases significantly since there are no metal lines which remain in such areas after endpoint.

An analog signal obtained from a sensor installed in a CMP machine platen is a continuous one, resulting from being scanned across the one or more wafers held by the carrier and the surface of the carrier in between the wafers. If the reflectivity and emissivity of the carrier surface is significantly different than that of the wafers, there is a significant discontinuity of the signal obtained by the photodetector as its view crosses an edge of the wafer. Discrete measurements of the wafer surface are referenced to these discontinuities as a way of identifying the positions of the measurements. In some cases it is desired to take specific measurements near an edge of the wafer outside of patterned circuit die, and in others it is desired to take specific measurements over a patterned location. Control of the location is made possible by use of the edge discontinuity. The measurements at specific positions of the wafers are then monitored over time in order to measure the effect of the processing on the wafer surface.

The representative features of the present invention described above can be implemented alone without use of the others but various combinations of the foregoing summarized features and others are alternatively combinable for use in specific applications. Additional features, advantages and objects of the various aspects of the present invention are included in the following description of various embodiments, which description should be taken in conjunction with the accompanying drawings.

BRIEF DESCRIPTION OF THE DRAWINGS

FIG. 1 schematically illustrates in general terms a system for optically scanning a substrate to monitor a characteristic of the substrate surface;

FIGS. 2 and 3 show, in cross-section, alternative versions of a general optical scanning head of FIG. 1;

FIG. 4 shows the primary components of a first specific embodiment of the optical scanning head of FIG. 1;

FIG. 5 is a cross-sectional view of the optical head of FIG. 4;

FIG. 6 shows the primary components, in cross-section, of a second specific embodiment of the optical scanning head of FIG. 1;

FIG. 7 shows a modified optical arrangement for the system of FIG. 1 to make measurements at two wavelengths;

FIG. 8 are exemplary curves of measurements made of a transparent film with two wavelengths according to the system of FIG. 1, as modified by the optics of FIG. 7;

FIG. 9 is a table that illustrates use of the curves of FIG. 8;

FIG. 10 shows another modified optical arrangement for the system of FIG. 1 that modulates the illuminating optical radiation source;

FIG. 11 shows another modified optical arrangement for the system of FIG. 1 that modulates illuminating optical radiation sources and makes measurements at two wavelengths, FIG. 12 is a curve of a measurement made of a metal film according to the system of FIG. 1;

FIG. 13 is a table that illustrates use of the curve of FIG. 12;

FIG. 14 is a side view of one type of CMP machine;

FIG. 15 schematically illustrates relative motion of various components of the CMP machine of FIG. 14;

FIGS. 16A and 16B are exemplary signals occurring in the CMP machine of FIGS. 14 and 15;

FIG. 17 schematically illustrates a further embodiment of a sensor with light source and fiberoptic output, where an instrument utilizes LEDs radiating light at different wavelengths, the source of electrical current, field lens, diffuser, focusing lens, fibers and fiber-optic couplers;

FIG. 18 is a schematic drawing of a system using a sensor according to FIG. 17, the system including a reference LED, polishing platen, pad, wafer, rotating feed-through, dichroic beam splitter, and detector circuit;

FIG. 19 schematically shows a sensor including optical paths of the light rays with optical aperture, bandpass filter, and photodetector;

FIG. 20 is a cross section of a silicon wafer coated with a multilayer structure of metal-oxide-metal and arranged in patterns with trenches;

FIG. 21A are curves showing calculated graphical dependencies of wafer emissivity with a 25% density pattern as a function of a metal film thickness;

FIG. 21B is another example of the calculated endpoint surface emissivity of Si wafer coated with 90% density pattern of Cu—Ta—$SiO_2$—Ta—Cu as a function of wavelength;

FIG. 22 depicts sample of a signal reflected from the structure of FIG. 20 at 660 nm recorded with a sensor according to FIG. 17 during polishing of the wafer; and FIG. 23 illustrates another embodiment of an optical sensor with a diffuser, light guide, and photodetectors for reflected and reference signals.

DESCRIPTION OF PREFERRED EMBODIMENTS

Referring initially to FIG. 1, a system utilizing the measurement techniques of the present invention is illustrated in general terms. A substrate or other object 11 contains a surface 13 that is being measured. An optical sensor head 15 directs optical radiation from one or more light emitting diodes (LEDs) against a spot 17 of the surface 13. Other sources of optical radiation can be used instead of LEDs but it is preferred that they have a narrow bandwidth, such as a few dozen nanometers in wavelength, or less. Highly coherent sources of optical radiation are unnecessary. A portion of the source radiation that is reflected from the surface is gathered by suitable optics, such as an optical fiber 19. Other optics, such as an optical fiber 21, collects a portion of the source radiation, preferably without any significant amount of radiation reflected from the surface, as background radiation that is used as a reference.

The sensor head 15 is connected with a module 23 that includes optical and electronic elements to interface between the sensor 15 and a host controller 25, such as a personal computer. Photodetectors 27 and 29 receive the optical signals from the optical fibers 19 and 21, respectively, to generate electrical signals in respective lines 31 and 33. These electrical signals are amplified by respective amplifiers 35 and 37, whose outputs are connected with an analog-to-digital converter 39. The amplified and digitized outputs of the photodetectors 27 and 29 and then sent to a controller 41 which controls operation of the sensor 15 and of the module 23, and can make a portion or all of the calculations necessary to determine the ultimate quantity related to the characteristic of the surface 13 that is being measured. The module 23 also includes a power circuit 43 that supplies, through a line 45, the LEDs or other optical radiation source included within the sensor head 15. The power is supplied by the host controller 25 but controlled by the controller 41. the module 23 is preferably provided in a small rugged package so that it may be positioned near the head 15 in a piece of processing machinery.

The size of the illuminated spot 17 is made to suit the measurement, a range of one-quarter to three-fourths of an inch in diameter for the applications specifically described herein. A diameter of the sensor head 15 of about one-half of one inch is preferred for the CMP applications described below, resulting in a spot 17 having a diameter something less than that, depending upon the optical elements at the end of the head 15. The size of the spot 17, of course, determines the area of the surface 13 that is averaged or integrated during each measurement.

Measurements can be made at a single point of the surface 13, at multiple points, or continuously across the surface 13, such as along a path 47, by providing relative motion between the head 15 and surface 13. Either the head 15 can be moved, or the substrate 11 moved, or both. In the CMP application described below, both are moved.

FIG. 2 shows a conceptual cross-sectional view of an end portion of the sensor head 15. Optical radiation from the source(s) (not shown in FIGS. 2 and 3) contained in the head 15 is directed through an optical radiation spreading element that extends across an end opening of a cylindrical housing 51. The element 49 spreads the source radiation over a maximum angle θ, preferably with substantially uniform intensity. A diffraction element may be made for this purpose but use of ground glass for the element 49 operates satisfactorily and provides a randomness to the surface illumination. As discussed above, better results are obtained as the angle θ increases. The element 49 is designed to provide this angle to be at least 45 degrees.

An end of an optical fiber has an acceptance angle of optical radiation that depends primarily upon the refractive index of the fiber core material. Such an angle Φ is shown on FIG. 2 at an end of the optical fiber 19, which extends through the element 49 to have an unobstructed view of the surface 13. It is also desirable that this angle be made as large as is practical, as discussed above, preferably 45 degrees or more. An optical fiber with a core made of sapphire, quartz or cubic zirconia has an angle of acceptance of about 45 degrees. For a larger angle Φ, or when other optical fiber cores with a lower refractive index are used, such as plastic, a lens element 53 can be added to the end of the optical fiber 19, as shown in FIG. 3. The diameter of the area viewed by the optical fiber 19 is increased, as indicated in FIG. 3. It is the area of the surface 13 within the angle of acceptance Φ that defines the spot 17, assuming that this area is also substantially uniformly illuminated.

One specific embodiment of a sensor head 15 is shown in FIGS. 4 and 5, where elements that are counterparts of those described above are identified by the same reference numbers but, when different in structure, have a prime (') added to the reference number. A plurality of LEDs 55–64 are distributed around a hemispherical shell 65. A transparent cover 67 may be provided with radiation scattering properties but a wide distribution of radiation results from the numerous LEDs and internal reflection within the shell 65. The surface 13 is illuminated with a range of angles close to 180 degrees, depending upon the distance between the shell and the surface 13. Lenses provided as part of the LEDs may also be roughened to add to the diffusion of the illumination provided by the head 15 of FIGS. 4 and 5.

Another specific embodiment of a sensor head 15, which is preferred, is shown in cross section in FIG. 6. Within the cylindrical shell 51 are a plurality of LEDs, including LEDs 71 and 73, carried by a flat plate extending across the inside of the shell. Radiation from the LEDs passes through a diffuser 77 through which the radiation gathering optical fiber 19 extends, similar to the structure of FIGS. 2 and 3. When used in hostile environments, such as in semiconductor liquid etch or CMP machines, the sensor head 15" is sealed against liquids, moisture and gas vapors. This can be done at one end by sealing the diffuser 77 to the diffuser 77 but a better seal is obtained by adding a single piece clear glass plate 79 which extends completely across and is sealed to the inside of the shell 51. Optical radiation from the LEDs is gathered into the optical fiber 17 by positioning a circular diffusive reflecting element 81 around the optical fiber 19. The element 81 is made small enough so as not to block the diffuser 77 from receiving almost all of the radiation from the LEDs but large enough to reflect enough of the radiation into the optical fiber 17 to obtain a useful background reference signal.

The wavelength of the optical radiation source is chosen to be the best for monitoring the particular surface characteristics of interest. The radiation needs to interact with the feature or characteristic of the object or its surface that is desired to be monitored, in a way that can be detected in the radiation after being modified by the object. For silicon semiconductor monitoring by reflecting radiation from a wafer, wavelengths slightly below the band edge of silicon are usually best, generally infra-red radiation less than one micron, to which the wafer is opaque. If radiation is transmitted through the object being monitored to obtain an object modified beam that is detected, the radiation is, of course, chosen to be of a wavelength that will pass through the object.

When the reflectivity of the surface 13 is being measured, the controller 41 calculates a ratio of the reflected radiation signal from the photodetector 27 to the background radiation signal from the photodetector 29, as is well known. The instrument is first calibrated by positioning the sensor head 15 against at least one surface having a known reflectivity, and preferably against several surfaces having known different reflectivities. Calibration includes adjusting the relative gains of the two signal channels until the instrument reads the known reflectivity of the test surface. This is preferably done by software within the controller 41, particularly when multiple test surfaces are used.

When the emissivity of the surface 13 is being measured, the controller subtracts the reflectivity from unity, as is well known. The instrument is similarly calibrated by using test order t surfaces of known emissivities. In the examples to follow, emissivity of a surface is calculated as a measure of the thickness of a layer of material that forms that surface.

The primary application is in semiconductor processing but the techniques are not so limited. As is well known, a changing thickness of a dielectric material, which is transparent to the incident radiation, is monitored by measuring the interference of the radiation reflected from both surfaces of the layer. The interference signal passes through peaks and valleys as the layer either becomes thicker when being formed by chemical vapor deposition (CVD) or otherwise, or becomes thinner as material is removed by wet or dry etching, CMP or some other technique.

The ability to determine an absolute thickness of a dielectric layer, rather than only a relative thickness or rate of change of the thickness, is provided by the present invention by making the measurement separately at different wavelengths and then combining the results. FIG. 7 shows a modification of the single wavelength embodiments described above. Two different types of LEDs 91 and 92 emit optical radiation at wavelengths λ1 and λ2, respectively. This is reflected off the surface 13 and gathered by an optical fiber 93, passed to a beam splitter 95 and thence to photodetectors 97 and 99 through respective optical bandpass filters 101 (λ1) and 103 (λ2). The signal outputs of these photodetectors are then digitized by the analog-to-digital converter 39'. The reference radiation is obtained by an optical fiber 105 which directs the radiation sampled from the LEDs 91 and 92 to a beam splitter 107. A portion of the reference radiation then strikes a photodetector 109 through an optical filter 113 that passes λ1, and another portion reaches a photodetector 111 through an optical filter 115 that passes λ2. The electrical outputs of these photodetectors are also applied to the analog-to-digital converter 39'.

The controller 41 (FIG. 1) now calculates the reflectivity or emissivity of the surface 13 separately for each of the radiation wavelengths λ1 and λ2. Calculated emissivity data are shown in curves of FIG. 8. These curves are the same when the layer is being increased in thickness as when it is being decreased. One interference curve 117 results from processing the signals from the λ1 receiving photodetectors 97 and 109, and a second interference curve 119 is obtained from the signals from the λ2 receiving photodetectors 99 and 111. The calculation of emissivity described above is made twice, once for each wavelength. The curves of FIG. 8 show the emissivity of an oxide layer with λ1=0.650 micron and λ2=0.740 micron. Additional data can be acquired for a third or more distinct wavelengths, thus giving one or more additional interference curves, but the complexity of implementing such a system generally outweighs the advantages of doing so. The periods of the curves 117 and 119 are different because of the different wavelengths at which the data is acquired. Their peaks and valleys are thus not aligned. This allows the thickness of the transparent layer of the surface 13 to be determined from the data forming both of the curves 117 and 119. The two values of the curves are unique for each value of layer thickness, at least over a significant range of thicknesses.

The table of FIG. 9 illustrates this. Each of the pairs of emissivity values for the two wavelengths corresponds to a specific thickness of the layer being monitored. For example, when the emissivity is calculated to be u and w for the respective wavelengths λ1 and λ2, it is known that the thickness of the layer is (A). This is also shown on the curves of FIG. 8. Similarly, a combination of values from the curves 117 and 119 of v and x gives a thickness (B). The table of FIG. 9 is empirically determined for a specific layer material. An instrument that is capable of measuring the thickness of two or more types of materials has a separate look-up table for each material. There may be up to one entry for each set of digital samples taken at one sample time by the analog-to-digital converter 39' (FIG. 7) of the four analog signal inputs from the photodetectors 97, 99, 109 and 111. As an alternative to use of such a table, a mathematical function relating the two emissivity readings to layer thickness may be formulated for each different type of layer material that the instrument is intended to measure.

Depending upon the particular range of layer thicknesses and specific wavelengths used, long sequences of pairs of emissivity readings can repeat themselves in the look-up table of FIG. 9, and thereby introduce an ambiguity in the thickness readings made. When this occurs, an additional piece of information is given the controller 41 (FIG. 1), such as the approximate thickness at the beginning of an etch or CMP process. The user can input this information when the process is begun. This then allows the controller to start with the proper thickness value in response to a pair of emissivity readings that occurs more than once in the table. Use of a third or more emissivity readings can eliminate the ambiguity in many cases. When the measurement is being made of the thickness of a layer being formed, it is known to start making readings in the look-up table at zero thickness, so any repeating sequences of values do not cause an ambiguous thickness calculation.

Depending on the wavelength(s) at which the measurements are made, ambient radiation can exist in the processing machine or environment in which the measurements are taken. This can, of course, affect the accuracy of the surface measurements. Although the measuring instrument can be shielded from such optical radiation in many cases, its effect can alternatively be effectively eliminated by modulating the incident radiation at a frequency other than that at which the ambient radiation may be modulated. That is, the power supply frequency and harmonics (60, 120 Hz. etc. in the U.S.) are avoided. Frequencies of any electrical noise generated in the processing machinery, which can be induced into the measurement circuits carrying low level signals, are also avoided. The photodetector output is then applied to an electronic bandpass filter to pass a narrow band of frequencies around the modulating frequency. Such a technique is shown in FIG. 10, wherein the power supply 43a to an LED 121 is modulated with a sinusoidal signal having a frequency f1, such as several hundred Hz., depending on the situation. Background and reflected radiation photodetectors 121 and 123 apply their electrical signal to respective amplifiers 127 and 129. The amplified signals are then passed through respective filters 131 and 133 having narrow pass bands around the frequency f1. The electrical outputs of the filters 131 and 133 therefore represent the optical signals resulting from illumination by the LED 121 without optical or electrical noise introduced by the environment. Some characteristic of the filtered alternating current signals, such as their root-mean-square (rms), is taken as representative of the surface characteristic being measured, before further arithmetic processing.

This LED modulation technique can also be adapted to serve an additional function in a multiple wavelength instrument, as a variation of the embodiment of FIG. 7. FIG. 11 shows LEDs 135 and 137, emitting optical radiation at respective distinct wavelengths λ1 and λ2, being modulated at respective distinct frequencies f1 and f2. Rather than using optical filters to obtain separate signals for each of the two wavelengths, as is done in FIG. 7, electrical bandpass filters are used. Only one reference radiation photodetector 139 is used, and only one photodetector 141 receives LED radiation reflected from the surface 13.

Photodetector outputs are amplified by pre-amplifiers 143 and 145. The amplified signal from the photodetector 139 is applied to two filters 147 and 149, which each pass narrow frequency bands around one of the LED modulating frequencies f1 and f2, respectively. Similarly, the amplified signal from the photodetector 141 is applied to two filters 151 and 153, which pass the frequencies f1 and f2, respectively. The four filter outputs are then digitized by the analog-to-digital converter 39*b*. The controller 41 (FIG. 1) then processes the signals from the f1 bandpass filters 147 and 151 to obtain data for one of the curves of FIG. 8, and also processes the signals from the f2 bandpass filters 149 and 153 to obtain data for the other curve. Thus, if the modulating frequencies f1 and f2 are both chosen to suppress optical and electrical environmental noise in the manner discussed above with respect to FIG. 10, the system of FIG. 11 has that advantage as well. Additionally, the systems of FIGS. 7 and 11 can be combined by using both optical and electrical filters.

The optical detection of films of normally opaque materials such as metals has typically been limited to determining when a breakthrough occurs during removal of the film by detecting when the amplitude of reflected radiation changes from one level to another in response to the metal being totally removed. However, as illustrated by the curve of FIG. 12, a measurement of the reflectivity or emissivity of a metal layer can provide a measurement of its thickness when very thin. The shape of the curve in FIG. 12 is for a copper layer over a layer of tantalum, as an example, the combination of which is carried by another material, usually a dielectric, on a substrate. Copper is used for conductors in integrated circuits. The layer of tantalum, or some other appropriate material, provides a barrier to prevent copper from diffusing into the underlying dielectric. The emissivity of the two layer structure, when at their full thicknesses, is a (FIG. 12), but when the copper layer is very thin, between thicknesses (X) and (Y), its emissivity varies in a measurable manner between a and b, as a function of its thickness. For copper, the thickness at (X) is about 1,000 Angstroms. In this example, the underlying tantalum is thin enough to not be completely opaque, its emissivity also varying in a measurable manner between levels b and c as a function of its thickness, as indicated between thicknesses (Y) and (Z) in FIG. 12. The emissivity c is that of the material under the tantalum, usually a dielectric.

Such thin layers of metal are becoming extensively used in semiconductor processing and structures. The techniques of the present invention may be used to measure thickness of thin metal layers in situ during their formation, thinning or complete removal from all or portions of a wafer. When copper is used for conductors, a dielectric layer is formed to cover the wafer except where contacts need to be made through the dielectric layer to aluminum, polysilicon, substrate diffusions and the like. Shallow trenches are formed in the dielectric to define where the copper conductors are to be placed. A thin (typically 200–800 Angstroms) barrier layer, such as tantalum, is then deposited over the entire dielectric, including the trenches and vias through the dielectric. A copper layer is then formed, usually by electroplating, over the barrier layer. CMP is then used to remove the copper and underlying barrier layer from the top surface of the dielectric, leaving them in the trenches and vias where the copper conductors are desired to remain.

FIG. 13 is a look-up table that provides empirically determined data relating the emissivity and layer thickness of the curve of FIG. 12. Measurements of emissivity, made by one of the ways described previously, are then converted to thickness by use of such a look-up table. The dual wavelength and modulated source techniques may also be used with metal layers.

It can be then seen that the thickness of a thin metal layer, when in a region such as between (X) and (Y) of FIG. 12, can be carefully controlled both during its formation and during its removal. When forming the two tantalum and copper layers of that example, the data of that characteristic curve are monitored from right to left, and when the layers are being removed, from left to right. It is also useful to monitor the thickness of a layer when it is being totally removed since this can give the process controller or the operator an indication when that end point is about to be reached.

A very significant application of the various aspects of the present invention is the in situ measurement of layer thickness during its removal, at least partially, by CMP. The largest application of CMP is in semiconductor wafer processing. There are many different types of CMP machines being used and contemplated for use in the future. They provide relative motion with pressure between the layer surface and a pad, with a slurry of liquid chemical etchant and abrasive particles between them. It is difficult to optically monitor processes of such machines in situ because of the complex motion usually given to the substrate and layer being measured, limited optical access and optically hostile environment.

FIGS. 14 and 15 show installation of a film thickness monitor according to the present invention on a CMP machine. In this example, four semiconductor wafers are being processed at one time. Wafers 161 and 163 carry respective layers 165 and 167 that are being reduced in thickness. The backsides of the wafers are attached to respective wafer carriers 169 and 171. The wafer carriers are rotated by respective electrical motors 173 and 175. A structure 177 holds the wafer carriers in position. The wafer layers are urged against a pad 179 that is attached to a round platen 181 that itself is rotated by an electrical motor 183. A layer 185 of a liquid chemical etchant and abrasive particles in a slurry is applied to the pad 179. Material is removed from exposed surfaces of the wafer layers 165 and 167 by grinding them across the pad 179 with the abrasive slurry between them.

The sensor head 15 described above, preferably the version shown in FIG. 6, is installed in the platen 181 in a position to look up to reflect light off of the layers being processed as they move over the head 15. A transparent window 187 is installed in the pad 179 over the sensor 15. Optical radiation generated within the head 15 then travels upward through the window 187, through the slurry 185, strikes the wafer layers in turn that are being processed, and returns back through the same path to the gathering optics within the head 15. The head electronics 23 is attached underneath the platen 181. Communication of its digital output signals and control signals with the host controller 25 can occur through a slip-ring assembly 189 on a rotating shaft 191 of the platen 181. Alternatively, wireless communication can be utilized, such as with the use of infra-red or radio frequency frequencies.

It can be seen that the optical path between the sensor head 15 and the wafer layer being monitored is not unencumbered. Particularly the slurry 185, although largely transparent to the interrogating radiation, affects the optical radiation that must pass through it twice, once in each direction. But the sensor head of the present invention overcomes this difficulty to provide good measurements. The wide angle radiation illumination and collection, as described above, minimizes adverse effects of the changing optical properties of the slurry over time, particularly changing radiation scattering. The present invention thereby makes it possible to accurately measure the thickness of the layers being processed, while they are being processed.

FIG. 15 shows the platen 181 with the position in space of the wafers 161 and 163, as well as additional wafers 162 and 164, shown in dotted outline. Each of the four wafers is rotated in the direction indicated with arrows by its individual driving motor. The direction of rotation of the platen 15 is also indicated by an arrow. The sensor head 15 is thus scanned in a path 193 across all four rotating wafers, one at a time. An example emissivity signal obtained from the sensor head electronics 23 (FIG. 1) is shown in FIG. 16A. This signal provides the emissivity (or, alternately, can be the reflectivity, if desired) of each wafer in turn as it is being scanned by the sensor 15, with the emissivity (or reflectivity) level of some other portion(s) of the CMP machine being measured as the sensor 15 moves between wafers. A rotational position encoder 195 attached to the rotating platen shaft 191 is read by a sensor 197, from which the host controller 25 generates relative position pulses such as those shown in FIG. 16B. The encoder and sensor 195 and 197 can be of any suitable mechanical, optical, magnetic or other known type. The position pulses have a purpose of allowing the host controller to correlate the received data with an individual wafer.

The host controller 25 can easily separate the stream of data obtained from the sensor head electronics 23, as shown in FIG. 16, into separate that from the wafers and that from the portions of the processing machine in between the wafers. This is because of a sharp change in emissivity level that will normally occur as the sensor head 15 passes across an edge of a wafer. For example, such a change occurs at a signal edge 201 as the sensor head 15 passes across an edge of the wafer 161 and onto the wafer. As the sensor head 15 leaves the wafer 161, passing from it to view some other surface, an edge 203 in the signal of FIG. 16A occurs. As the processing of the wafer 161 proceeds, the measured level of its emissivity changes, for example, between two levels 205 and 207. Because the edges of the wafers are defined in the signal, this allows the host controller 25 to select a location on the wafer a certain distance from an edge for measuring emissivity as the processing proceeds. A signal 209 is indicated for a given wafer location a defined distance from a wafer edge. This wafer location can be selected, for example, to be where integrated circuits are formed, or, alternatively, nearer wafer edges where integrated circuits are not formed. The signal 209 varies over time, in a manner of the examples of FIGS. 8 and 12. Each time the sensor head 15 passes over the location of the waver 161 where the signal 209 is taken, a new emissivity data point is acquired for that location. Monitored data may be selected by the host controller 25 for each of the other three wafers that have the same position with respect to their edges as the data 209 of the wafer 161. By using such a common location, the layer thickness may be compared among wafers.

Of course, data for more than one location on each wafer may be monitored during the processing. Averages of several data points across each wafer may also be independently monitored. Or an average of all readings across a specific segment or the entire wafer can be made and turned into time based signals of the type shown in FIGS. 8 and 12. Further, as can be seen from the signal of FIG. 16A, uniformity of the processing across a defined portion or all of the individual wafers can be monitored. Non-uniform processing shows as a variation of the data 205 in a single span, for example, between the edges 201 and 203. Statistical calculations can be made by the host processor 25 of data from a particular wafer to provide an indication of a spread of the emissivity values across that wafer, either from a single scan or from multiple scans across it. Further, polishing rates may be calculated from the emissivity data, either at one or more specific wafer locations with respect to an edge or on the average across a portion or the entire wafer.

It will be recognized from FIG. 15 that the path 47 (FIG. 1) scanned across a wafer is not the same each time because of the complex relative motion given to the wafers and the sensor head 15. That motion, however, depends upon the particular CMP equipment with which the measuring techniques of the present invention are utilized.

Further Optical Sensor and Processing Embodiments

FIG. 17 shows a schematic diagram of another optical sensor 511 with application to CMP. Illuminating optical radiation 522 is delivered from one or more sources 520 (for example LEDs) contained within a cylindrical housing and is directed toward a surface under investigation 532 through an opening in the housing by a lens 524 positioned there across. The optical radiation 522 then passes through a random diffuser 526 and a transparent window 528 provided in a polishing platen 530 of a CMP machine, and onto a surface 532 of a semiconductor wafer or other article being processed. The combined effect of the radiation sources 520, the lens 542, the diffuser 526 and the close position of the diffuser 526 to the window 528, and thus the to surface 532, produces predominantly uniform illumination of the surface 532 within a very broad range of angles. Incident radiation is reflected by the surface 532 and is directed back through another area of the lens 524, another lens 534 onto thence to an input aperture 536 of a photodetector or fiberoptic coupler 538. An angle of spread of the radiation reflected from the surface 532 and accepted by the aperture 536 is much narrower in this embodiment than the angles of incidence of radiation rays scattered by the diffuser 526.

While the diffuser in the embodiment of FIG. 17, because of its close position with respect to the surface of interest 532, illuminates that surface with rays extending over an angle much in excess of 45 degrees, such as 80 degrees or more, the angle of rays of the reflected radiation collected by the lens 534 into the aperture 536 extends over significantly less than 45 degrees, such as less than 25 degrees. As described further below, this narrow collection angle improves the depth of focus of the collection optics, which improves the measurement results in environments where the distance between the surface 532 and the collection optics varies, such as is the case in many CMP machines. The use of a very large angle of illumination allows the collection angle to be made this narrow and still provide accurate emissivity measurements.

Two or more LEDs 520 radiating at different wavelengths are positioned inside the circular perimeter 540 of the sensor housing. One optical aperture 536 is positioned within the housing about 180 degrees therearound from a corresponding LED 520 so that reflected radiation 542 will be predominantly directed from each LED into a corresponding receptor (photo-detector or fiber optic end). The arrangement illustrated in the drawings utilizes 2 LED sources radiating in spectral bands centered around 660 nm and 880 nm, respectively, but different spectral sources, including a continuous incandescent light source, may be used if it is beneficial for the intended monitoring of the surface 532, such as the thickness of a film on that surface and endpoint diagnostics.

The illustrated optical arrangement serves multiple purposes:

1. It uniformly distributes incident radiation over the area of the surface 532 being measured. This minimizes alteration of intensity of the incident radiation with variations of the gap between the sensor and the polished surface;

2. It provides predominantly uniform irradiation of the surface within the broad range of incident angles. This allows compensation for scattering and diffraction components of radiation reflected during emissivity measurements of surfaces with the patterned structures;

3. It allows to extract a narrow beam of radiation deflected or scattered from a small portion of the surface 532 and redirect it into an input aperture of a photodetector or a fiber-optic coupler. An accurate surface emissivity measurement results from a combination of items 2 and 3;

4. It provides significant depth of focus for the portion of the surface being analyzed. That makes sensor less sensitive to the gap variation between the surface and detector, and 5. It offers flexibility to accommodate various radiation sources with different spectral bands. Emissivity of the surface measured at several spectral bands allows eliminating ambiguity in film thickness determination.

FIG. 18 shows an instrument utilizing the optical sensor 511 in a polishing tool. The sensor 511 is placed inside a polishing platen 544 which is typically rotated at a speed of 10–100 rpm, about a center of rotation 545. During a full revolution of the platen 544, the sensor 511 passes by and monitors the surfaces of semiconductor wafers 546 and 547, which are pressed against the platen and held in place by means of respective rotating wafer carriers 548 and 549. A single wafer can alternatively be processed and monitored at one time, or more than two wafers may be simultaneously processed with more than two wafer carriers. The LEDs 520 within the sensor 511 are energized by means of a power stabilizing circuit 550 carried by the platen 544 in a position close to the sensor 511 in order to minimize the effect of electrical interference. Electrical power is fed through wires extending from an outside power source 552, through a rotating electrical current feed-through 554, to the circuit 550 and thence to the sensor 511. Alternatively, a portable battery may be attached to the platen 544.

The radiation of the LEDs that is reflected from the wafer surface is transmitted through several optical fibers 556 that each have a core diameter between 0.002–1.0 mm., in a specific example. A separate radiation source 558 within the sensor 511 of FIG. 18 (not shown in FIG. 17) emits a different spectral band from that of the LEDs 520 or its emission is modulated at a unique frequency to provide a reference signal. The optical fibers 556 are further connected to one fiber 560 through a coupler 557. The optical fiber 560 carries the optical signal reflected from the wafer surface and collected by multiple apertures 536. The fiber 560 is connected through an optical feed-through 562 that is coaxial with the electrical coupler 554. The optical signal is further transmitted to a photo-detector module, which converts radiation intensity for each spectral band into a corresponding electrical signal. In the example shown, multiple dichroic beam splitters 564 are used with corresponding multiple photodetectors 565 and an electrical current amplifier 566 for each spectral band (actually shown). Alternatively, a photodetector with an amplifier and frequency demodulation circuit may be used, or combination of those. The electrical signal is further conditioned, digitized, and processed by means of computer 568 or digital signal processor board.

Although the delivery of optical signals through optical fibers physically connected between the sensor 511 and the photo-detector module off the platen 544 of FIG. 18 requires an additional rotational coupler 562, this arrangement has the advantages of delivering signal free from electrical interference, a compact sensor design and increased reliability. Other types of wireless data communication between the rotating sensor 511 and the stationary photo-detector module may alternatively be used, such as radio, acoustic and optical radiation communication links.

Since the rotation of the platen 544 can cause vibration and bending of the coupling optical fibers and the fiber-optic coupler to affect the reflected optical signals, and since the electrical signals can be modulated by strong electrical interference, it can be desirable to use a reference signal having a magnitude proportional to that of the input radiation that is subject to the same uncontrolled variations. The processing system separates the reference signal from the reflected signal by modulation at a different frequency or use of a different wavelength. In the example system of FIG. 18, the reference radiation from the separate spectral source 558 with different wavelength than that of the LEDs 520 is combined in single fiber with the reflected signals by means of the optical fiber connection module 557. The reference signal then follows the same path as the reflected signals and experiences the same modulation from varying optical conditions and electrical interference. The dichroic beam splitter 564 separates the reference signal from the reflected signals for further processing. The emissivity of the surface 532 is found from a ratio of the power of the input radiation incident upon the surface 532 to that of the output signal measured by the photo-detectors 565, after combination with a calibration factor. The thickness of a film on the surface 532 may be determined from its emissivity, as one application of the system being described, in order to monitor its removal. Determination of an end point removing a film by CMP is a primary application of the system described.

FIG. 19 is an expanded and more detailed view of the optical system of the sensor 511 of FIGS. 17 and 18. The radiation rays emitted from the radiation source (LEDs) 520 fill an aperture of the lens 524. The lens 524 is placed at approximately its focal length f1 from the surface 532 being monitored. In this arrangement, a set of parallel rays incident on the lens will focus on the above surface. Since the radiation source 520 radiates in substantial cone of angles $\alpha$, the focused radiation on the surface would occupy spot of the size d1, where d1=$\alpha \times$f1.

The diffuser 526 operates to spread the radiation rays 522 over the spot with a size of d1. The purpose of the diffuser is to provide more uniform surface illumination simulating that of radiating hemisphere. The diffuser covers only part of the lens 524 aperture. The rest of the aperture is clear. The clear portion of the lens collimates the radiation 542 reflected from the spot on the surface, into a collimated beam 523. A portion of the collimated radiation subsequently passes through the second lens 534 positioned at its focal length f2 from the input aperture 536 of fiber-optic coupler or photo-detector 539. The size of the aperture 536 d2 determines the projected size of the spot on the surface 532. This optical system has low numerical aperture and big depth of focus. Together with uniform broad angle surface illumination, it assures high stability of the reflected signal when the distance between the surface 532 and the sensor aperture 536 varies, within several millimeters, as the platen 544 rotates. This feature is important for industrial applications, since the polishing tool and the sensor are subjected to vibrations, altering applied pressure, varying slurry conditions, wear of the polishing pad over time, all of which may change distance between the surface under investigation and the sensor. This minimizes errors in the surface measurements that can occur over time in the CMP machine.

As a variation in the specific sensor 511 described above, detectors with pinhole apertures and narrow-band filters can replace the fiberoptic components.

FIG. 20 schematically illustrates an example of a silicon wafer 570 coated with a multilayer structure that is arranged in so-called "device" patterns 578. The example shown in an expanded cross section 580 through a device on the wafer 570 includes a stack of metal and dielectric layers. Specifically, in this example, layers of Cu—Ta—$SiO_2$—Ta—Cu within trenches 576 in a $SiO_2$ layer are filed with a layer of copper on top of it. Other arrangements and materials may be actually used depending on manufacturing process. A spacing 586 between "devices" on the wafer 570 represent blank areas (typically less then 500 microns wide) left for future cutting of the wafer to separate the devices (dies) into separate integrated circuit chips. During the CMP process, a layer of slurry 572 is usually applied to the top layer 582, which is also rubbed by the polishing pad of the rotating platen. The optical sensor 511 continuously monitors emissivity of the wafer through the window 528 of the polishing pad (FIGS. 17 and 18). The spacing between the copper (Cu) filled trenches 576 in the patterned area is in a sub-micron range. This spacing may be as little as one tenth of a micron in the case of so-called "high density device" wafers, where trenches occupy bigger part of the surface. In that case, the surface is highly reflective, even after completely clearing the top Cu layer 584 to the endpoint level 574, where the Cu layer 584 is totally removed except for that remaining in the trenches 576, since the Cu filled trenches will continue to reflect most of the incident radiation. As a result, the average change in the emissivity of such a wafer when the endpoint is reached is low and the endpoint is therefore difficult to measure.

The optical sensor 511, however, overcomes this difficulty by measuring the emissivity of the surface at the small localized spot (typically less then 500 microns) at a high data rate (1–100 kHz) sufficient enough to detect changes in the local wafer emissivity. When the optical sensor 511 moves from "device" area 578 to an open space 586 between device, the reflected signal amplitude changes proportionally to the change in reflectivity between the pattern area 580 of a device and the area 586 in between the devices that does not contain trenches. In case of "high density device" wafers, this change may constitute up to 90% of the total amplitude. When the areas between devices are monitored, the change in detected signal level as the metal is removed to the endpoint 574 is large since there are no trenches in these areas 586 that retain metal as there are in the devices 578 themselves. As a result, the signal of reflection from the clear areas 586 remains relatively unchanged at the beginning of the polishing cycle, and exhibits a strong and fast alteration in level later in time close to reaching the endpoint.

FIG. 21B demonstrates graphically a calculated example of changes in the emissivity of the wafer as a top metal film is removed. The calculation assumes a semiconductor having a cross-sectional structure that is similar to that shown in FIG. 20, with the surface being monitored having metal filled trenches occupying 25% of the device area. The initial height of Cu was assumed to be 1000 Angstroms, the height of the interlaying Ta being 150 Angstroms, the height of the Si oxide layer being 4000 Angstroms, and a trench depth of 2000 Angstroms. The height on the graph is marked from the top boundary of the Cu—Ta interface. In this way, the value of zero along the horizontal axis corresponds to the position of the endpoint line 574 on the FIG. 20. As is shown, the emissivity values 590 (one curve for each of two different illumination wavelengths, as shown) may experience significant changes during wafer polishing and is used as a threshold for the endpoint condition. This is especially true for wafers with homogeneous blanket layers. On the other hand, as it was mentioned before, wafers with "high density device" pattern tend to reduce the scale of emissivity changes. In the example shown, when trench density increases from 25% to 90%, peak emissivity at 880 nm will go down from 0.723 to 0.145 with the starting level of 0.06, and at 660 nm from 0.145 to 0.129 with the starting level of 0.11. This example also illustrates importance of using appropriate wavelength for the emissivity measurements since it is subjected to the effect of thin-film interference.

The curves of FIG. 21B provide an example of the calculated surface emissivity of a coated Si wafer as a function of interlayer Si oxide thickness at different wavelengths, as an example of one of many dielectrics that can be used. In the example shown, a wafer is assumed to have a cross-sectional structure similar to that shown in FIG. 20 but with a the metal filled trenches 576 occupying 90% of the device surface area (a 90% trench density pattern). It was found that for every selected wavelength, there is an interlayer thickness which tends to obscure changes of emissivity during removal of the top layer. As can be seen from a curve 592, when the optical sensor operates at 650 nm, it is insensitive to layer breakthrough with Si dioxide interlayer thickness at around 1900 Angstroms and 4200 Angstroms (points 594 of the curve 592). At the same time, a sensor operating at 950 nm (curve 596) is insensitive to layer breakthrough at around 3000 Angstroms (point 598), but produces significant changes at 1900 Angstroms and 4200 Angstroms. This means that measuring emissivity at several wavelengths is desirable in many circumstances for reliable endpoint detection. For example, combining detectors operating at 650 nm and 950 nm or 850 nm will be sufficient for the considered layer structure to reliably detect the endpoint when an interlayer Si dioxide thickness is in a 500–6000 Angstrom range. Other wavelength combinations can be used depending on the wafer manufacturing process.

FIG. 22 depicts sample of emissivity signal recorded during polishing of the Cu coated wafer with device pattern similar to one shown in FIG. 20. It can be noted from FIG. 22 that the emissivity 600 experiences strong amplitude modulation during the clearing of the top metal layer as the sensor 511 scans over the semiconductor surface being processed. The amplitude of signal modulation along with average signal changes 602 may be used to detect the endpoint condition. Use of the highly localized surface spot for emissivity measurements provides an increased difference in signal amplitude between the device pattern areas and the open spaces between devices, and increases the sensitivity of the sensor to remaining metal film thickness. As a result, the optical sensor 511 described above demonstrates a significant advantage in endpoint detection.

FIG. 23 illustrates an alternative sensor configuration. Two radiation beams 522 are emitted from spectral sources 520, which may operate at different wavelengths and/or modulation frequencies. The radiation of each beam is further scattered by a respective diffuser 608 to simulate broad angle uniform illumination. A clear aperture 610 between the diffusers 608 allows radiation reflected from the surface 530 to be directed through an optical fiber or other light guide 604 to a photodetector 606. The intensity of the reflected signal is compared with the output of the radiation source 520 as measured by separate photodetector 612 or a current supply circuit to the source 520. A circuit 614 further enhances and amplifies the ratio or other combination of these two photo-detector signals. The combination signal is processed by a digital signal processor or some other computer means. This signal, after application of a calibration factor, allows finding the emissivity of the surface 532 being measured.

Although the various aspects of the present invention have been described with respect to their preferred embodiments, it shall be understood that the invention is entitled to protection within the full scope of the appended claims.

What is claimed is:

1. Apparatus for determining in situ a reflective characteristic of an area of a surface of an article being processed, comprising:
    a machine component having a surface adapted to contact said article surface,
    a window forming a portion of said component surface,
    at least one source of optical radiation provided on the machine component on a side of the window opposite to the article contacting surface,
    an optical radiation spreading element carried by the machine component between the window and said at least one source of optical radiation, said element spreading light from said at least one source of optical radiation through the window over an angle of 45 degrees or more,
    collection optics carried by the machine component in a position to gather optical radiation passing through said window after reflection by the article area,
    a photo-detector receiving optical radiation from the collection optics to generate an electrical signal related thereto, and
    a processor utilizing the electrical signal to determine the reflective characteristic of the article area.

2. The apparatus of claim 1, wherein the collection optics is characterized by gathering optical radiation through said window over an angle of 45 degrees or more.

3. The apparatus of claim 1, wherein the collection optics is characterized by gathering optical radiation through said window over an angle of 15 degrees or less.

4. The apparatus of claim 3, wherein the optical spreading element is characterized by spreading light through the window over an angle of 80 degrees or more.

5. The apparatus of claim 1, wherein the collection optics includes a first light pipe that extends through the spreading element with an end facing the window, and wherein the apparatus further includes a second light pipe having an end positioned between said at least one source of optical radiation and the spreading element to obtain optical radiation from said at least one source of optical radiation.

6. The apparatus of claim 5, wherein the article contacting surface of the component is planar and has a back surface defining a thickness of the element therebetween, and wherein all of the window, at least one source of optical radiation the spreading element, the second optical radiation spreading element, the first light pipe end, and the second light pipe end are positioned in a compartment formed in the component between its said article contacting and back surfaces.

7. The apparatus of claim 5, additionally comprising a second optical radiation spreading element carried by the component between the window and said at least one source of optical radiation in a position to direct optical radiation from said at least one source of optical radiation into the second light pipe end.

8. The apparatus of claim 6, wherein an electronic unit is attached to said machine component that includes amplifiers for each of the first and second electrical signals, an analog-to-digital converting circuit, and a processor, an output of the processor providing data of the article area reflective characteristic being determined.

9. The apparatus of any one of the claims 1–8, wherein the component is part of a chemical-mechanical-polishing machine that is given motion while processing the article area.

10. The apparatus of claim 9, wherein the component is a platen with a polishing pad as its said surface adapted to be contacted by said article.

11. The apparatus of claim 9, wherein the processor is characterized by providing an indication of an emissivity of the article surface area.

12. The apparatus of any one of claims 1–4, wherein at least two sources of optical radiation are provided at different optical wavelengths, the photo-detector receives optical radiation form the collection optics in said different optical wavelengths, and the processor utilizes signals from both of the optical wavelengths to calculate the article surface area reflective characteristic.

13. The apparatus of claim 12, additionally comprising circuits driving said at least two sources of optical radiation with different modulating frequencies, and electrical band-pass filters receiving the photo-detector signal to distinguish components modulated at said modulating frequencies.

14. The apparatus of claim 12, wherein the surface area reflective characteristic calculated by the processor is an indication of an emissivity of the article surface area.

15. The apparatus of claim 1, wherein said at least one sources of optical radiation includes a plurality of radiation sources positioned across a reflective inside surface of a hemispherically shaped shell that opens onto said optical radiation spreading element.

* * * * *